(12) United States Patent
Gallopyn et al.

(10) Patent No.: US 11,881,302 B2
(45) Date of Patent: Jan. 23, 2024

(54) VIRTUAL MEDICAL ASSISTANT METHODS AND APPARATUS

(71) Applicant: Nuance Communications, Inc., Burlington, MA (US)

(72) Inventors: Guido Gallopyn, Haverhill, MA (US); Reid W. Coleman, Rehoboth, MA (US)

(73) Assignee: Microsoft Technology Licensing, LLC., Redmond, WA (US)

( * ) Notice: Subject to any disclaimer, the term of this patent is extended or adjusted under 35 U.S.C. 154(b) by 280 days.

(21) Appl. No.: 16/680,213

(22) Filed: Nov. 11, 2019

(65) Prior Publication Data
US 2020/0243186 A1 Jul. 30, 2020

Related U.S. Application Data

(63) Continuation of application No. 13/782,438, filed on Mar. 1, 2013, now Pat. No. 10,504,622.

(51) Int. Cl.
*G16H 40/20* (2018.01)
(52) U.S. Cl.
CPC .................. *G16H 40/20* (2018.01)
(58) Field of Classification Search
CPC ..................................................... G16H 40/20
See application file for complete search history.

(56) References Cited

U.S. PATENT DOCUMENTS

| | | |
|---|---|---|
| 4,696,039 A | 9/1987 | Doddington |
| 5,031,113 A | 7/1991 | Hollerbauer |
| 5,051,924 A | 9/1991 | Bergeron et al. |
| 5,680,511 A | 10/1997 | Baker et al. |
| 5,758,322 A | 5/1998 | Rongley |
| 5,787,394 A | 7/1998 | Bahl et al. |

(Continued)

FOREIGN PATENT DOCUMENTS

| | | | |
|---|---|---|---|
| JP | 2010148559 A | * | 7/2010 |
| WO | WO 2006/014851 A1 | | 2/2006 |

(Continued)

OTHER PUBLICATIONS

N. Matsumoto and A. Tokosumi, "A Reference of Intentions for Better Medical Communication," 2007 IEEE/ICME International Conference on Complex Medical Engineering, 2007, pp. 453-456 (Year: 2007).*

(Continued)

*Primary Examiner* — Sheetal R Paulson
(74) *Attorney, Agent, or Firm* — Barta, Jones & Foley, PLLC

(57) ABSTRACT

In some aspects, a method of using a virtual medical assistant to assist a medical professional, the virtual medical assistant implemented, at least in part, by at least one processor of a host device capable of connecting to at least one network is provided. The method comprises receiving free-form instruction from the medical professional, providing the free-form instruction for processing to assist in (Continued)

identifying from the free-form instruction at least one medical task to be performed, obtaining identification of at least one impediment to performing the at least one medical task, and inferring at least some information needed to overcome the at least one impediment.

20 Claims, 8 Drawing Sheets

(56) References Cited

U.S. PATENT DOCUMENTS

| | | | |
|---|---|---|---|
| 5,909,667 | A | 6/1999 | Leontiades et al. |
| 5,999,896 | A | 12/1999 | Richardson et al. |
| 6,003,002 | A | 12/1999 | Netsch |
| 6,073,101 | A | 6/2000 | Maes |
| 6,173,259 | B1 | 1/2001 | Bijl et al. |
| 6,212,498 | B1 | 4/2001 | Sherwood et al. |
| 6,360,237 | B1 | 3/2002 | Schulz et al. |
| 6,366,882 | B1 | 4/2002 | Bijl et al. |
| 6,418,410 | B1 | 7/2002 | Nassiff et al. |
| 6,434,547 | B1 | 8/2002 | Mishelevich et al. |
| 6,463,413 | B1 | 10/2002 | Applebaum et al. |
| 6,487,530 | B1 | 11/2002 | Lin et al. |
| 6,567,778 | B1 | 5/2003 | Chao Chang et al. |
| 6,813,603 | B1 | 11/2004 | Groner et al. |
| 7,383,172 | B1 | 6/2008 | Jamieson |
| 8,781,829 | B2 * | 7/2014 | Koll .............. G06F 3/167 704/235 |
| 9,478,218 | B2 | 10/2016 | Shu |
| 10,504,622 | B2 | 12/2019 | Gallopyn et al. |
| 2002/0040282 | A1 | 4/2002 | Bailey et al. |
| 2005/0033574 | A1 | 2/2005 | Kim et al. |
| 2007/0033026 | A1 | 2/2007 | Bartosik et al. |
| 2007/0208567 | A1 | 9/2007 | Amento et al. |
| 2008/0091464 | A1 * | 4/2008 | Lipscher .......... G06Q 40/08 705/2 |
| 2008/0202978 | A1 | 8/2008 | Salomon et al. |
| 2008/0255835 | A1 | 10/2008 | Ollason et al. |
| 2009/0192800 | A1 * | 7/2009 | Brandt .......... G16H 20/10 704/270.1 |
| 2010/0049756 | A1 | 2/2010 | Chemitiganti et al. |
| 2012/0173281 | A1 | 7/2012 | DiLella et al. |
| 2013/0041685 | A1 | 2/2013 | Yegnanarayanan |
| 2013/0085781 | A1 | 4/2013 | Navani et al. |
| 2013/0311190 | A1 | 11/2013 | Reiner |
| 2014/0047375 | A1 | 2/2014 | Koll et al. |
| 2014/0074454 | A1 * | 3/2014 | Brown .............. G06F 3/167 704/235 |
| 2014/0249830 | A1 | 9/2014 | Gallopyn et al. |
| 2014/0249831 | A1 | 9/2014 | Gallopyn et al. |
| 2015/0302536 | A1 * | 10/2015 | Wahl .............. G06Q 50/00 705/2 |
| 2019/0046126 | A1 | 2/2019 | Owen et al. |
| 2019/0051376 | A1 | 2/2019 | Gallopyn et al. |
| 2019/0051377 | A1 | 2/2019 | Owen et al. |
| 2019/0051386 | A1 | 2/2019 | Owen et al. |
| 2019/0051387 | A1 | 2/2019 | Owen et al. |
| 2019/0066821 | A1 | 2/2019 | Owen et al. |

FOREIGN PATENT DOCUMENTS

| | | |
|---|---|---|
| WO | WO 2007/050541 A2 | 5/2007 |
| WO | WO 2009/091585 A1 | 7/2009 |

OTHER PUBLICATIONS

European Communication for European Application No. 14709149.0 dated Sep. 26, 2018.

International Search Report and Written Opinion for International Application No. PCT/US2014/018478 dated May 6, 2014.

Aronow et al., Ad Hoc Classification of Radiology Reports. Journal of the American Medical Informatics Association. 1999;6(5):393-411.

Bateman et al., The Quest for the Last 5%: Interfaces for Correcting Real-Time Speech-Generated Subtitles. Interactive Posters. CHI 2000. 2 pages.

Birnbaum et al., Report: A Voice Password System for Access Security. AT&T Technical Journal. 1986. 7 pages.

Bisani et al., Automatic Editing in a Back-End Speech-to-Text System. Proceedings of ACL-08: HLT. 2008:114-20.

Carbonell, Foreword of "Automatic Ambiguity Resolution in Natural Language Processing: Am Empirical Approach." Springer 1996. 1 page.

Heng-Hsou et al., An Event-Driven and Ontology-Based Approach for the Delivery and Information Extraction of E-mails. IEEE. 2000. 103-9.

Hewitt et al., Real-Time Speech-Generated Subtitles: Problems and Solutions. ISCA Archive. 6th International Conference on Spoken Language Processing (ICSLP 2000). 2000. 5 pages.

Mendonca et al., Extracting information on pnemonia in infants using natural language processing of radiology reports. Journal of Biomedical Informatics. 2005;38:314-21.

Naik, Speaker Verification: A Tutorial. IEEE Communications Magazine. 1990:42-8.

Newman et al., Speaker Verifcation Through Large Vocabulary Continuous Speech Recognition. Dragon Systems, Inc. 1996. 4 pages.

Peng et al., p. 336 of the Conference Proceedings "Natural Language Processing and Information Systems: 12$^{th}$ International Conference on Applications of Natural Language to Information Systems, NLDB 2007, Pairs, France, Jun. 27-29, 2007".

Rosenberg, Evaluation of an Automatic Speaker-Verification System Over Telephone Lines. Manuscript received Sep. 9, 1975. The Bell System Technical Journal. 1976;55(6):723-44.

Shvaiko et al., Ontology Matching OM-2008. Papers from the ISWC Workshop. 2008. 271 pages.

Sistrom et al., Managing Predefined Templated and Macros for a Departmental Speech Recognition System Using Common Software. Journal of Digital Imaging. 2001;14(3):131-41.

Soderland et al., Automated Classification of Encounter Notes in a Computer Based Medical Record. MEDINFO 1995 Proceedings. 1995 IMIA. 9 pages.

Sonntag et al., A Discourse and Dialogue Infrastructure for Industrial Dissemination. German Research Center for AI (DFKI). Proceeding IWSDS'10 Proceedings of the Second international conference on Spoken dialogue systems for ambient environments. 2010. 12 pages.

Sonntag et al., RadSpeech's Mobile Dialogue System for Radiologists. IUI'12. 2012. 2 pages.

Suhm, Multimodal Interactive Error Recovery for Non-Conversation Speech User Interfaces. Dissertation. 1998. 292 pages.

Taira et al., Automatic Structuring of Radiology Free-Text Reports. infoRAD. Radiology 2001;21:237-45.

\* cited by examiner

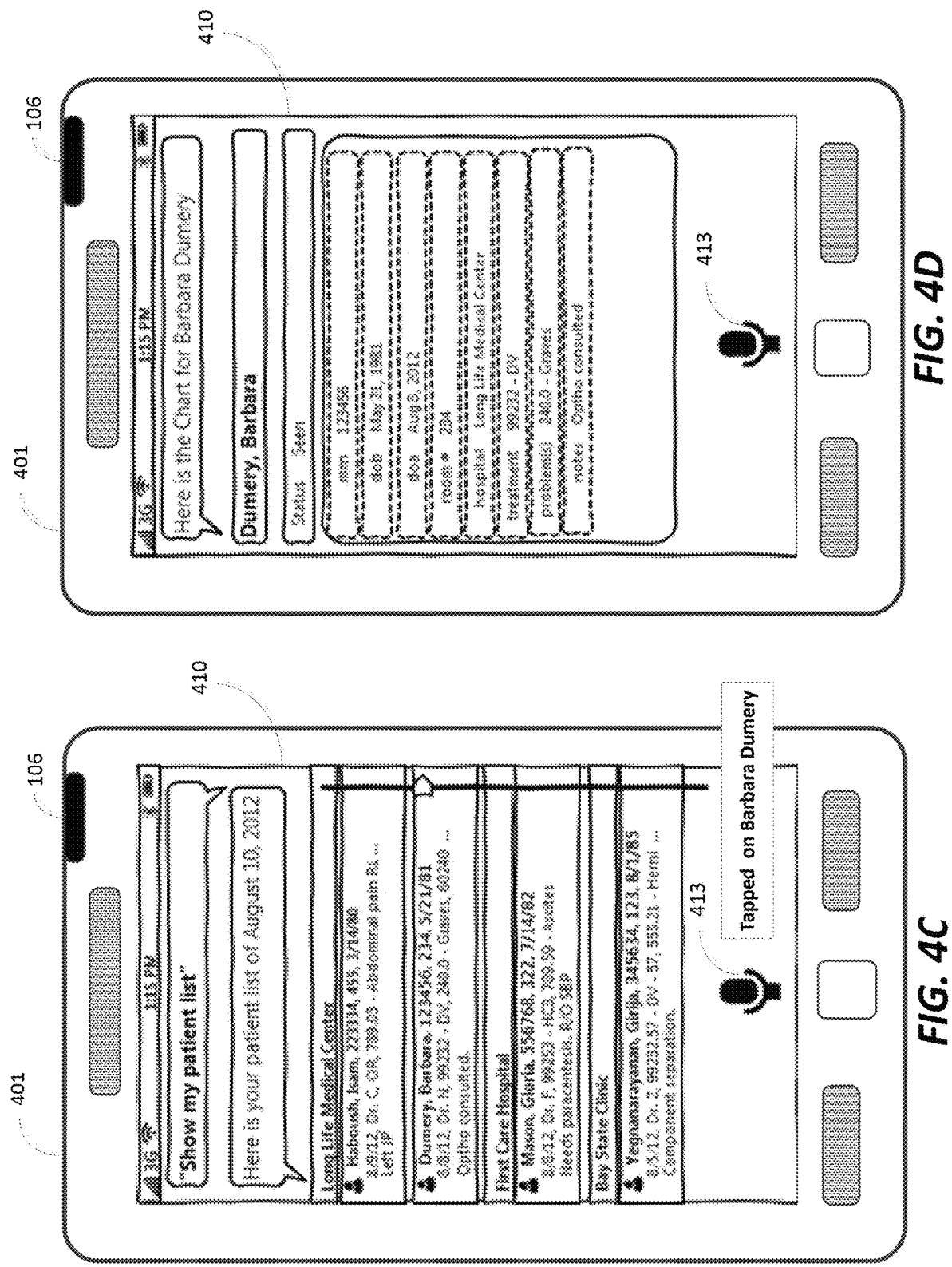

VIRTUAL MEDICAL ASSISTANT METHODS AND APPARATUS

This Application is a Continuation of U.S. application Ser. No. 13/782,438, filed Mar. 1, 2013, entitled "VIRTUAL MEDICAL ASSISTANT METHODS AND APPARATUS". The entire contents of these applications are incorporated herein by reference in their entirety.

BACKGROUND

Many mobile communications devices, such as smart phones, are equipped with a virtual assistant (also referred to as a virtual agent) configured to receive speech input from a user and employ various resources, either locally or accessible over a network, to recognize the user's speech, attempt to understand the user's intent and respond by performing one or more desired tasks based on that understanding (e.g., perform an internet search, make a telephone call, schedule an appointment, etc.). However, conventional virtual assistants are configured to respond to voice commands of the general user and therefore may be limited in their capabilities, often focusing on general information retrieval, personal scheduling or engaging communication functionality on the mobile device (e.g., initiating a phone call, sending a text or email message to an individual in the user's contact list, etc.).

SUMMARY

Some embodiments include a method of using a virtual medical assistant to assist a medical professional, the virtual medical assistant implemented, at least in part, by at least one processor of a host device capable of connecting to at least one network, the method comprising receiving free-form instruction from the medical professional, providing the free-form instruction for processing to assist in identifying, from the free-form instruction, at least one medical task to be performed, providing at least one first response to the medical professional regarding the free-form instruction prior to the at least one medical task being performed, and receiving first information from the medical professional responsive to the at least one first response.

Some embodiments include at least one computer readable medium storing instructions that, when executed by at least one processor, performs a method of using a virtual medical assistant to assist a medical professional, the virtual medical assistant implemented, at least in part, by at least one processor of a host device capable of connecting to at least one network, the method comprising receiving free-form instruction from the medical professional, providing the free-form instruction for processing to assist in identifying, from the free-form instruction, at least one medical task to be performed, providing at least one first response to the medical professional regarding the free-form instruction prior to the at least one medical task being performed, and receiving first information from the medical professional responsive to the at least one first response.

Some embodiments include a host device capable of connecting to at least one network, the host device comprising at least one processor implementing, at least in part, a virtual clinical assistant to assist a medical professional, the at least one processor configured to, receive free-form instruction from the medical professional, provide the free-form instruction for processing to assist in identifying, from the free-form instruction, at least one medical task to be performed, provide at least one first response to the medical professional regarding the free-form instruction prior to the at least one medical task being performed, and receive first information from the medical professional responsive to the at least one first response.

Some embodiments include a method of using a virtual medical assistant to assist a medical professional, the virtual medical assistant implemented, at least in part, by at least one processor of a host device capable of connecting to at least one network, the method comprising receiving free-form instruction from the medical professional, providing the free-form instruction for processing to assist in identifying from the free-form instruction at least one medical task to be performed, obtaining identification of at least one impediment to performing the at least one medical task; and inferring at least some information needed to overcome the at least one impediment.

Some embodiments include at least one computer readable medium storing instructions that, when executed on at least one processor, perform a method of using a virtual medical assistant to assist a medical professional, the virtual medical assistant implemented, at least in part, by at least one processor of a host device capable of connecting to at least one network, the method comprising receiving free-form instruction from the medical professional, providing the free-form instruction for processing to assist in identifying from the free-form instruction at least one medical task to be performed, obtaining identification of at least one impediment to performing the at least one medical task, and inferring at least some information needed to overcome the at least one impediment.

Some embodiments include a host device capable of connecting to at least one network, the host device comprising at least one processor implementing, at least in part, a virtual medical assistant to assist a medical professional, the at least one processor configured to receive free-form instruction from the medical professional, provide the free-form instruction for processing to assist in identifying from the free-form instruction at least one medical task to be performed, obtain identification of at least one impediment to performing the at least one medical task, and infer at least some information needed to overcome the at least one impediment.

BRIEF DESCRIPTION OF DRAWINGS

Various aspects and embodiments of the application will be described with reference to the following figures.

FIGS. 4A-4H illustrate examples of interaction between a virtual medical assistant application installed on a mobile device and a medical professional using the mobile device, in accordance with some embodiments.

DETAILED DESCRIPTION

Figure 1:
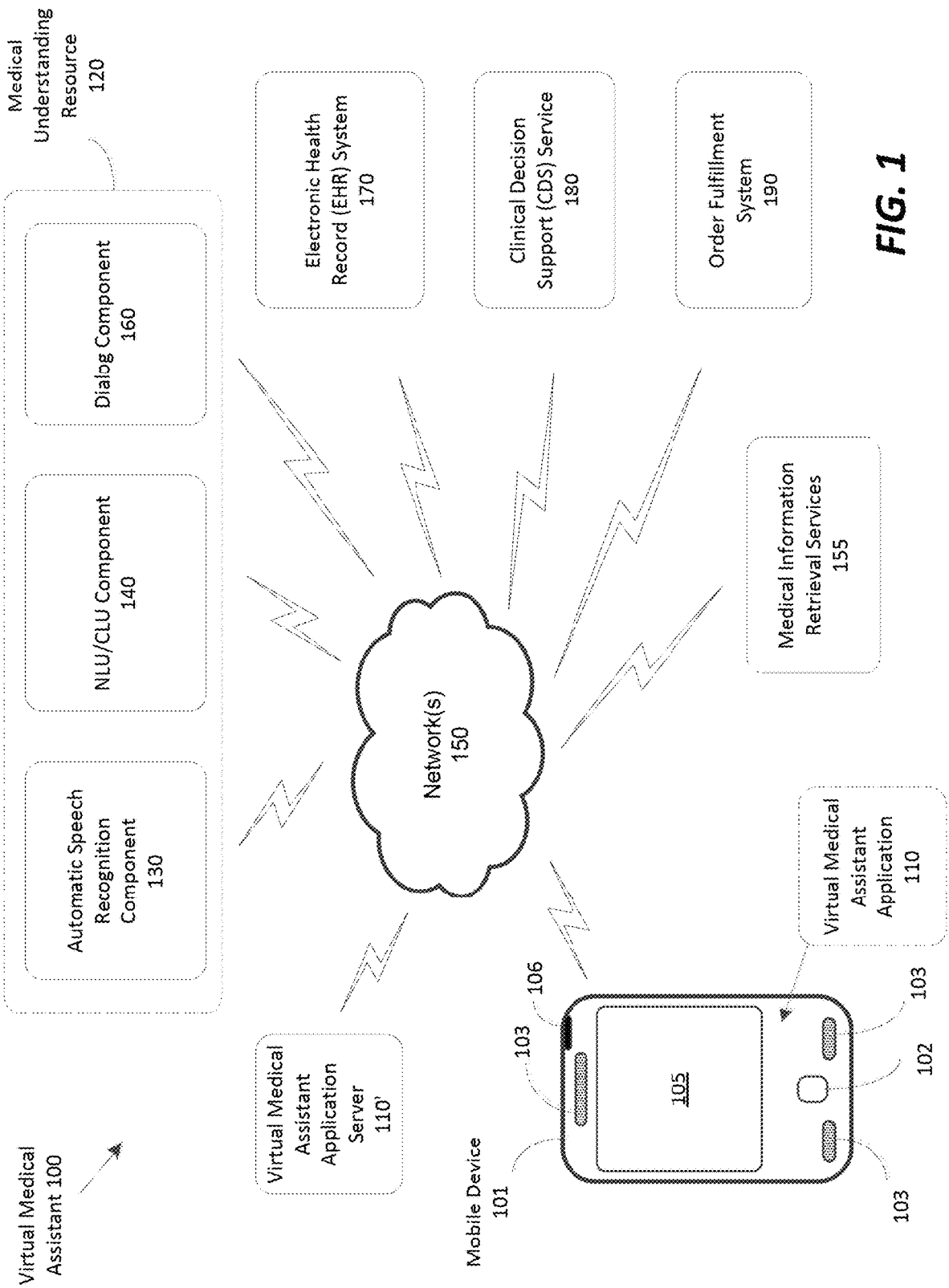
FIG. 1 illustrates an exemplary system in which a virtual medical assistant may be implemented, in accordance with some embodiments.

As discussed above, conventional virtual assistants are frequently adapted to be useful to a broad range of users and therefore are generally limited to performing generic, and often very few, tasks in response to user commands. Conventional virtual assistants may therefore be unsuitable for performing specialized tasks. The inventors have appreciated the benefit of a virtual assistant adapted for the medical domain to assist a medical professional in performing actions or tasks in the context of the medical professional's medical practice and/or health care capacity. Such a domain specific virtual assistant may be capable of performing functionality within the medical domain that are beyond the reach of conventional virtual assistants.

According to some embodiments, a virtual medical assistant is implemented, at least in part, on a host device and is configured to assist a medical professional in performing one or more medical tasks including, but not limited to, assisting a medical professional in ordering an orderable item (e.g., a medication, a procedure, lab results, a diagnostic test, a referral, a consultation, etc.), identifying conflicts, accessing and displaying patient information, capturing dictation corresponding to a patient encounter, updating an electronic medical record (EMR) of a patient, scheduling a patient visit, obtaining medical information, etc. Details of a virtual medical assistant according to some embodiments are provided below.

The term "virtual medical assistant" refers herein to one or more computer implemented components (e.g., software components, hardware components, or a combination of both) configured to receive input from a medical professional, initiate appropriate processing of the input to identify one or more medical tasks specified by the input and/or initiate one or more processes to facilitate performance of the one or more identified medical tasks specified by the input. A medical professional refers herein to a person qualified in the practice of medicine, psychiatry, or psychology, including, but not limited to, general physicians, surgeons, psychiatrists, psychologists, therapists, or other licensed health care professionals.

The inventors have recognized benefits of a virtual medical assistant implemented, at least in part, on a host device operated by a medical professional, wherein the virtual medical assistant is configured to receive free-form instruction from the medical professional and to facilitate processing of the free-form instruction to identify and/or assist in performing one or more medical tasks that the medical professional specified in the free-form instruction. Free-form means that a medical professional is generally unconstrained with respect to the structure and/or content of the provided instruction. As such, a medical professional may provide instruction using natural conversational language that need not (but may) conform to any particular command grammar and/or command lexicon, and have at least some instructions understood by the virtual medical assistant. Accepting free-form instruction allows a virtual medical assistant to be utilized without requiring a medical professional to first learn a set of structured commands to be understood by the virtual medical assistant. The term "instruction" refers herein to any actionable input including, but not limited to, one or more commands, requests, queries, questions, inquiries, etc. Some examples of free-form instruction are discussed in further detail below to illustrate various concepts related to virtual medical assistant methods and apparatus.

As discussed above, the inventors have recognized benefits of a virtual medical assistant capable of receiving free-form instruction and processing the free-form instruction to identify one or more medical tasks specified in the free-form instruction. Some medical tasks performed by a medical professional may be relatively complicated in that they often require certain information to be specified fully and in a particular manner in order for the medical task to be performed. In addition, some medical tasks relate to the health and well-being of a patient and care must be taken to ensure the safety and suitability of certain medical tasks to be performed. The inventors have appreciated that a virtual medical assistant that can interact with a medical professional via a dialog exchange may facilitate more efficient performance of certain medical tasks. In addition, discourse between the virtual medical assistant and the medical professional may relieve some of the burden from the medical professional of correctly and safely carrying out one or more medical tasks that a medical professional would like performed.

According to some embodiments, a virtual medical assistant is configured to receive free-form instruction from a medical professional and initiate processing to identify one or more medical tasks specified in the free-form instruction. The virtual medical assistant may provide, via the host device or other interface device, at least one response in connection with the free-form instruction prior to the one or more medical tasks being performed. The response provided by the virtual medical assistant may include, for example, a request for additional information, a request for clarification and/or disambiguation regarding the one or more identified medical tasks, one or more alerts or warnings with respect to a conflict in connection with the one or more identified medical tasks, a confirmation regarding the one or more identified medical tasks, an inquiry as to whether the medical professional would like to proceed, or any other comment, question or inquiry regarding the free-form instruction.

As discussed above, it may be inconvenient or time consuming for a medical professional to specify every detail regarding a medical task to be performed. In addition, some medical tasks require certain information to be specified fully and in a specific manner before the task can be performed, making it relatively burdensome for a medical professional to accomplish certain medical tasks. According to some embodiments, a virtual medical assistant infers at least some information needed to perform one or more medical tasks identified in free-form instruction from a medical professional using information available to the virtual medical assistant. For example, the virtual medical assistant may infer information from one or more previously received free-form instructions from the medical professional, information obtained in performing one or more previous medical tasks, patient information from an electronic medical record (EMR) associated with a patient and/or information obtained from one or more medical information resources accessible over a network.

Accordingly, a virtual medical assistant so configured may be capable of assisting a medical professional in performing one or more medical tasks specified in free-from instruction from the medical professional, and may facilitate doing so even in the presence of incomplete, ambiguous, inconsistent and/or conflicting instruction from the medical professional by obtaining further information from the medical professional and/or inferring information based on data accessible to the virtual medical assistant. The virtual medical assistant may also (or alternatively) be configured to provide information to the medical professional that may be useful to the medical professional in completing one or more medical tasks, such as by identifying conflicts and/or providing one or more alerts or warnings, providing confirmation regarding a medical task to be performed, etc., as discussed in further detail below.

Following below are more detailed descriptions of various concepts related to, and embodiments of, methods and apparatus for implementing a virtual medical assistant. It should be appreciated that various aspects described herein may be implemented in any of numerous ways. Examples of specific implementations are provided herein for illustrative purposes only. In addition, the various aspects described in the embodiments below may be used alone or in any combination, and are not limited to the combinations explicitly described herein.

FIG. 1 illustrates a system 100 within which a virtual medical assistant may be implemented, according to some embodiments. The virtual medical assistant comprises a virtual medical assistant application 110 implemented, at least in part, by one or more processors of a mobile device 101. Virtual medical assistant application 110 may be installed as one or more software components on mobile device 101, for example, by downloading the virtual medical assistant application as an "app" via a network, or otherwise installing the application on mobile device 101. Virtual medical assistant application 110 may be configured to access and utilize one or more network resources communicatively coupled to the virtual medical assistant 110 via one or more networks 150 (e.g., via network communication capability available on the host device).

Virtual medical assistant application 110 and one or more network resources accessed by the virtual medical assistant application 110 are collectively referred to herein as the virtual medical assistant. Thus, actions described as being performed by the virtual medical assistant are to be understood as being performed by the virtual medical assistant application 110 and/or any one or combination of network resources accessed, utilized or delegated to by the virtual medical assistant application 110, example resources of which are described in further detail below in connection with the system illustrated in FIG. 1. Thus, according to some embodiments, a virtual medical assistant may be implemented as a distributed system having at least some functionality implemented on a host device (e.g., mobile device 101) and at least some functionality implemented via one or more network resources.

In FIG. 1, the virtual medical assistant may be accessed by a medical professional using mobile device 101 via virtual medical assistant application 110 installed, at least partially, on the mobile device as discussed above. Mobile device 101 in FIG. 1 is illustrated as having a number of components characteristic of a "smart phone," but it should be appreciated that mobile device 101 may be any suitable host device capable of receiving input from a user (e.g., a medical professional), providing information (e.g., rendering information to a user visually, audibly, etc.), and communicating with network resources via one or more networks, as the aspects are not limited for use with any particular type of host device.

In particular, in addition to mobile devices, suitable host device types include personal computers or other generally stationary or fixed computing devices accessible by the medical professional. Another alternative to hosting a virtual medical assistant includes one or more network accessible computers that are accessed using telephony, wherein the network computer(s) hosts the virtual medical assistant and the functionality is accessed via a separate interface device. For example, a medical professional may call into a system capable of accessing one or more host devices using any suitable telephony device and conduct interactions with the virtual medical assistant using speech, such that the interface device (e.g., the telephony component used by the medical professional) interacts with, but does not itself necessarily host, the virtual medical assistant. Such a telephony-based implementation may be accessed via the telephony capabilities of a mobile device (e.g., using cellular technology), or may be accessed using any other suitable telephony component).

Mobile device 101 may include one or more transducers 103 for converting acoustic energy to electrical energy and vice versa. For example, transducers 103 may include one or more speakers and/or one or more microphones arranged on the mobile device to allow input/output (I/O) of acoustic information. Different mobile devices may include differing numbers and arrangements of transducers, any of which may be suitable to facilitate acoustic I/O. Mobile device 101 may include further I/O functionality including display 105 for visually presenting information to the user. Display 105 may also be configured as an input device, for example, by responding to touch, pen input, etc. Mobile device 101 may include one or more other input components that allow a user to interface with the mobile device. For example, button 102 may be used as a selection button or may include any other functionality on the mobile device. Mobile device 101 may include a keypad (not shown), arrow buttons or any other input component capable of receiving input from a user, such as a medical professional using the mobile device to interact with virtual medical assistant application 110.

Mobile device 101 may also include one or more wireless communication components 106. For example, mobile communication devices such as cellular telephones will typically have a wireless transceiver capable of communicating with one or more cellular networks. Alternatively, or in addition to, wireless communication component 106 may include a wireless transceiver capable of communicating with one or more other networks or external devices. For example, wireless communication component 106 may include a component configured to communication via the IEEE 802.11 standard (Wi-Fi) to connect to network access points coupled to one or more networks (e.g., local area networks (LANs), wide area networks (WANs) such as the internet, etc.), and/or wireless communication component 106 may include a Bluetooth® transceiver to connect to a Bluetooth® compatible device, etc.

To simplify the illustration of exemplary mobile device 101, wireless communication component 106 is used to represent schematically any wireless communication component implemented on mobile device 101 and may include one or multiple components that may be either separate or integrated components, may be independent system components, or may be different system components in communication with one or more other wireless components. That is, wireless communication component 106 denotes one or any combination of components that may be implemented on a mobile device that allows the mobile device 101 to communicate wirelessly with one or more networks, systems and/or other devices. It should be appreciated that mobile device 101 is merely an example of a mobile device suitable for hosting a virtual medical assistant application and/or for use with any one or combination of virtual medical assistant techniques described herein.

Techniques described herein are not limited for use with any particular device having any particular number or arrangement of components, and any network aware device having I/O functionality may be suitable to operate as the host device for a virtual medical assistant application to access functionality of a virtual medical assistant. As discussed above, for example, the host device may be a personal computer or other standalone computer having network access (e.g., either wired, wireless, or combination, access to one or more networks), may be a network computer capable of being accessed by telephony components, or any other suitable computing device.

According to some embodiments, virtual medical assistant application 110 is configured to present one or more interfaces to receive input (e.g., free-form instruction from a medical professional) via the I/O functionality of the host device (e.g., mobile device 101). For example, virtual medical assistant application 110 may be configured to receive speech from a medical professional via one or more microphones coupled to mobile device 101, and initiate processes to recognize and understand the content of a medical professional's speech, as discussed in further detail below. Alternatively, or in addition to, virtual medical assistant application 110 may receive input from the medical professional in other ways, such as via any of the input mechanisms provided on mobile device 101 (e.g., touch sensitive display, keypad, mouse, one or more buttons or any other interface control provided on the host device). According to some embodiments, virtual medical assistant application 110 is configured to provide a graphical user interface (GUI) on display 105 of mobile device 101 that presents to the medical professional the mechanisms by which the medical professional may provide input to the virtual medical assistant.

Virtual medical assistant application 110 may also be configured to present one or more interfaces to provide information to the medical professional. For example, virtual medical assistant application 110 may display information to the user via the display on the host device (e.g., via a GUI displayed on a display 105 on mobile device 101). Virtual medical assistant application 110 may also provide information audibly to the medical professional, for example, using speech synthesis techniques and rendering synthesized speech via one or more speakers coupled to mobile device 101, or by rendering prerecorded speech or one or more sounds configured to convey information to the medical professional. According to some embodiments, virtual medical assistant application 110 is capable of rendering information to the medical professional both visually and audibly. Virtual medical assistant application 110 may include other mechanisms for providing information to the medical professional, as the aspects are not limited for use with any particular type or technique for providing and/or rendering information to the medical professional.

According to some embodiments, a virtual medical assistant may employ a virtual medical assistant application server 110' coupled to network(s) 150 to communicate with virtual medical assistant application 110 installed on mobile device 101 to assist with interfacing with one or more network resources. By implementing at least some functionality of the virtual medical assistant on virtual medical assistant server 110', the computer footprint of the virtual medical assistant application 110 installed on the host device may be reduced (e.g., on a mobile device where resources may be limited to some extent). However, in some embodiments, virtual medical assistant application server 110' may not be implemented and functionality to interface with the one or more network resources may be implemented by virtual medical assistant application 110 resident on the host device, as the aspects are not limited in this respect.

According to some embodiments, the virtual medical assistant may not include a virtual medical assistant application installed on the interface device used by the medical professional to access the functionality of the virtual medical assistant. For example, according to some embodiments, a medical professional may access the virtual medical assistant via a telephony device that does not host, or may be unsuitable for hosting, virtual medical assistant application software, and may interact with the virtual medical assistant via the telephony device. In such an implementation, the virtual medical assistant application may be implemented by one or more network computing devices accessible, either directly or indirectly, by the telephony device (e.g., virtual medical assistant application server '110 may implement all, or some portion, of the virtual medical assistant application functionality), and virtual medical assistant functionality may be delivered by network components to the interface device used by the medical professional.

According to some embodiments, virtual medical assistant application 110 is configured to access, utilize and/or delegate to one or more network resources coupled to network(s) 150, thus forming a virtual medical assistant (denoted generally as virtual medical assistant 100 in the example in FIG. 1) configured to assist in performing medical tasks requested by or on behalf of a medical professional. Network(s) 150 may be any one or combination of networks interconnecting the various network resources including, but not limited to, any one or combination of LANs, WANs, the internet, private networks, personal networks, etc. The network resources depicted in FIG. 1 are merely exemplary, and a virtual medical assistant may comprise any one or combination of network resources illustrated in FIG. 1, or may utilize other network resources not illustrated, as techniques described herein are not limited for use with any particular number or configuration of network resources.

As depicted in FIG. 1, virtual medical assistant 100 includes a medical understanding resource 120 comprising automatic speech recognition (ASR) component 130, natural language understanding (NLU) and/or clinical language understanding (CLU) component 140, and dialog component 160. Each of these components may be implemented in software, hardware, or a combination of software and hardware. Components implemented in software may comprise sets of processor-executable instructions that may be executed by one or more processors of one or more network computers, such as a network server or multiple network servers. Each of ASR component 130, NLU/CLU component 140 and dialog component 160 may be implemented as a separate component, or any combination of these components may be integrated into a single component or a set of distributed components implemented on one or multiple network computers (e.g., network servers). In addition, any one of ASR component 130, NLU/CLU component 140 and dialog component 160 may be implemented as a set of multiple software and/or hardware components. As such, processing described as being performed by medical understanding resource 120 refers to processing performed by any one or combination of the constituent components, operating alone or in concert with other constituent components.

The system illustrated in FIG. 1 also comprises a number of medical resources including electronic health record (EHR) system 170, medical decision support (CDS) service 180, order fulfillment system 190 and medical information retrieval services 155, each of which are discussed in further detail below. It should be appreciated that the network resources illustrated in FIG. 1 are merely exemplary and a virtual medical assistant may utilize one or any combination of resources illustrated, or may utilize other resources not illustrated or described. It should be further appreciated that the various components illustrated in FIG. 1 may be coupled in any suitable manner, and may be components that are located on the same physical computing system(s) or separate physical computing systems that can be coupled in any suitable way, including using any type of network, such as a local network, a wide area network, the internet, etc.

As discussed above, virtual medical assistant application 110 may receive input (e.g., free-form instruction from a medical professional) in the form of speech, and ASR component 130 may be utilized to identify the content of the speech (e.g., recognize the constituent words in the speech input). In particular, a medical professional may speak free-form instruction to the host device (e.g., mobile device 110) and/or an interface component capable of accessing, directly or indirectly, the host device. Virtual medical assistant application 110 may receive the free-form instruction from the medical professional and provide the free-form instruction to ASR component 130 to be recognized. The free-form instruction may be processed in any suitable manner prior to providing the free-form instruction to ASR component 130. For example, the free-form instruction may be pre-processed to remove information, format the free-form instruction or modify the free-from instruction in preparation for ASR (e.g., the free-form instruction may be formatted to conform with a desired audio format and/or prepared for streaming as an audio stream or prepared as an appropriate audio file) so that the free-form instruction can be provided as an audio input to ASR component 130 (e.g., transmitted over a network).

ASR component 130 may be configured to process audio input (e.g., audio input representing free-form instruction) to form a textual representation of the audio input (e.g., a textual representation of the constituent words in the free-form instruction that can be further processed to understand the meaning of the constituent words). Such processing to produce a textual representation may be performed in any suitable way. In some embodiments, ASR component 130 may convert speech to a representation other than a textual representation, or the speech may not be recognized as words, but instead a sequence or collection of abstract concepts. It should be appreciated that the words and/or concepts represented in the medical professional's free-form instruction may be represented and/or stored as data in any suitable form, as aspects are not limited in this respect. ASR component 130 may transmit the recognized free-form instruction over the network to be received by the virtual medical assistant application 110 (e.g., for display to the medical professional) and/or ASR component 130 may provide the recognized free-form instruction to one or more other network resources for further processing (e.g., the recognized free-form instruction may be provided to a NLU/CLU component 140 to assist in understanding the semantic content of the free-form instruction to identify one or more medical tasks specified therein), as discussed in further detail below.

According to some embodiments, ASR component 130 may be tailored, at least in part, to the medical domain. For example, ASR component may make use of a lexicon of medical terms (which may be part of, or in addition to, another more general speech recognition lexicon) while determining the sequence of words that were spoken in the free-form instruction from the medical professional. However, aspects of the invention are not limited to the use of a lexicon, or any particular type of lexicon, for ASR. When used, the medical lexicon in some embodiments may be linked to a knowledge representation model (e.g., a medical language understanding ontology, one or more statistical models and/or one or more rule-based models) utilized by NLU/CLU component 140 and/or dialog component 160, such that ASR component 130 produces a textual representation of the free-form instruction containing at least some terms in a form understandable to NLU/CLU component 140 and/or dialog component 160.

In some embodiments, ASR component 130 may use a more general speech recognition lexicon shared between ASR component and one or more other network resources. However, in other embodiments, ASR component 130 may not have any lexicon developed to be in common with the other exemplary network resources illustrated in FIG. 1 or otherwise described. In some embodiments, a lexicon used by ASR component 130 may be linked to a different type of medical knowledge representation model, such as one not designed or used for language understanding. It should be appreciated that any lexicon used by ASR component 130 (or any of the other network resources) may be implemented and/or represented as data in any suitable way. ASR component 130 may utilize one or any combination of suitable acoustic models, lexicons, grammars, language models, etc. to perform recognition, as aspects are not limited for use with any particular ASR implementation.

As discussed above, the medical understanding resource 120 may include NLU/CLU component 140 configured to process free-form instruction to identify one or more medical tasks specified in the free-form instruction and may also identify one or more parameters associated with the one or more medical tasks. According to some embodiments, a virtual medical assistant is configured to process free-form instruction from the medical professional. To this end, NLU/CLU component 140 may be designed to be relatively robust with respect to its ability to identify tasks in free-form instruction provided in as many of the myriad ways in which a medical professional might choose to express the instruction to the extent desired or to the extent reasonable (or possible). However, there is no limitation on what expressions an NLU/CLU component 140 may be capable of understanding, as implementations according to some embodiments may be more limited than others in this respect.

NLU/CLU component 140 may use any suitable language understanding techniques to ascertain the meaning of the free-form instruction so as to assist in identifying one or more tasks specified therein. For example, NLU/CLU component may be configured to identify and extract grammatical and/or syntactical components of the free-form speech, such as parts of speech, or words or phrases belonging to known semantic categories, to facilitate an understanding of the free-form instruction. For example, NLU/CLU component 140 may identify action words (e.g., action words that a medical profession may be inclined to use in specifying certain medical task), subject words, topic words, medical terms, clinical facts and/or any other type or category of words the NLU/CLU component 140 may deem relevant to ascertaining the semantic form or content of the free-form instruction to facilitate identifying medical tasks specified therein.

To assist in identifying medical tasks in free-form instruction, NLU/CLU component 140 may have specialized functionality tailored to the medical domain. For example, NLU/CLU component 140 may include one or more knowledge representation models that captures semantic knowledge regarding language in general and/or medical language in the specific. For example, a knowledge representation model may be capable of associating medical terms with corresponding categories, classifications or types. Such categories may include, but are not limited to, medications, allergies, procedures, diagnostic tests, laboratory tests, conditions, disease or disorders, symptoms, vital signs, anatomy, body sites, medical devices, observable findings, measurable findings, etc. It should be appreciated that the above list is merely exemplary, and some embodiments may not use one or more of the above-listed categories, and some embodiments may use other suitable categories.

A knowledge representation model may make use of or incorporate a formal ontology linked to a lexicon of medical terms. The formal ontology may be implemented as a relational database, or in any other suitable form, and may represent semantic concepts relevant to the medical domain, as well as linguistic concepts related to ways the semantic concepts may be expressed in natural language. Medical terms in the lexicon may be linked to at least one concept in the formal ontology.

A knowledge representation model may use, employ or implement one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. For example, in the context of a virtual medical assistant, the input on which the model operates may correspond to free-form instruction (or a representation derived therefrom) and the output may include an identification of a medical task specified by the free-form instruction and/or one or more associated parameters.

To supply the probabilistic data that allows a statistical model to extrapolate from the tendency of particular input characteristics to be associated with particular outputs in past examples, statistical models are typically trained (or "built") on training corpuses with relatively large numbers of example inputs. Typically, the example inputs are labeled with the known outputs with which they should be associated (e.g., a corpus of free-form instruction input may be labeled with the correct medical task the instruction specifies), often by a human labeler (e.g., with expert knowledge of the domain), or sometimes automatically. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output, for example, by a human), the statistical model can then use the learned probabilities for the extracted features (as learned from the training data) to determine which output is most likely correct for the new input. In the context of a virtual medical assistant, the features may correspond to the words, concepts, associations, relationships, etc. identified in the free-form instruction, and the statistical model may determine which one or more tasks is most likely correct for free-form speech received from the medical professional based on these features and their relationships.

A knowledge representation model utilized by NLU/CLU component 140 may also include (or alternatively include) one or more rule-based models that provide a set of rules as to how to map words or phrases in free-form instruction to corresponding medical tasks and/or that map words or phrases in free-form instruction to parameters of an identified medical task. For example, NLU/CLU component 140 may include a rule-based natural language processing system to extract medical facts, link facts to concepts or otherwise assist in identifying one or more medical tasks specified in free-form instruction received from a medical professional. In a rule-based system, a linguist and/or other individual may create a plurality of rules that can specify what words or combinations or words evidence that free-form speech specifies a particular medical task (e.g., an instruction to order an orderable item). Rule-based techniques can be employed by NLU/CLU component 140 to identify one or more medical tasks specified in free-form instruction from the medical professional (e.g., a request for patient information, instruction to place an order for an orderable item, instruction to take dictation, command to update a patient record, inquiry regarding a medical entity, etc.) and/or any parameters associated with identified medical tasks.

It should be appreciated that an NLU/CLU component may utilize one or any combination of techniques described above to identify medical tasks in free-form instruction and/or identify any parameters associated with identified medical tasks, as aspects are not limited for use with any particular technique or combination of techniques. In accordance with one embodiment described herein, a hybrid approach is used in which NLU/CLU component 140 employs both a statistical model and a rules-based component to identify one or more medical tasks specified in free-form instruction. Such a hybrid approach can be implemented in any of numerous ways, as aspects that employ a hybrid approach are not limited to any particular implementation technique. In accordance with some embodiments, the statistic model and rules-based component of the NLU/CLU component 140 may operate in parallel on the same free-form instruction, and in some embodiments they may operate serially. In either parallel or serial operation, the statistic model and the rules-based component may operate independently or may exchange information to facilitate identifying medical task(s) specified in free-form dictation, and/or parameters associated with a medical task.

According to some embodiments, a rules-based component may perform a first pass on free-form instruction to identify semantic entities by, for example, extracting medical facts, linking words or phrases into concepts, and/or identifying other characteristics of known medical tasks. Thereafter, the statistical model may be used to process the semantic entities to determine what one or more medical tasks the free-form instruction most likely relates to. That is, the outputs of the rules-based component can be used as features for the statistical model. For example, when a rule fires or otherwise indicates that the rule has been met, this may be a feature evaluated by the statistical model. Some rules may be quite specific, so that a firing of the rule indicates with high probability that the determination expressed thereby is accurate (e.g., detection of the word "order" in combination with identifying the name of a medication in the free-form instruction may indicate with high probability that the medical professional would like the virtual medical assistant to order the medication).

According to some embodiments, a statistical model may operate to identify the one or more medical tasks most likely specified by the free-form instruction and the rule-based component may be used to identify one or more parameters from the free-form instruction associated with the identified medical task. A statistical model and a rule-based component may be used in other suitable ways, as the aspects are not limited in this respect. In accordance with some embodiments, a determination can be made about whether to use a statistical model or a rule-based component depending upon the content of the free-form instruction. For example, some instructions that are very structured may lend themselves to rules, whereas types of instructions with significant variability in how they are expressed in natural language may be better suited to the use of a statistical model.

In accordance with some embodiments, an ontology of the type described above can be used in conjunction with a statistical model in any of numerous ways. For example, the use of an ontology can reduce the amount of annotated data that can be used in training the statistical model, as the ontology can demonstrate a number of alternate ways of expressing the same concept. Thus, it may not be necessary to include annotated data representing all of the alternate ways of expressing instruction to perform certain medical tasks, and the ontology can be combined with the statistical model to expand its ability to recognize alternative expressions not included in the annotated training data. Of course, this is merely one use of an ontology, as the ontology can be used in any suitable manner.

Again, the descriptions provided above for combining the use of a rule-based component with a statistical model and optionally with an ontology are merely illustrative, as the techniques described herein are not limited to any particular implementation techniques. The techniques described herein can be implemented using solely a statistical model, solely a rule-based component, or any combination, as they are not limited to any particular implementation technique. That is, processing by NLU/CLU component 140 may be as simplistic or as sophisticated as desired to suitably identify one or more medical tasks when they are present in free-form instruction provided by a medical professional.

As mentioned above, medical understanding resource 120 illustrated in FIG. 1 also may include dialog component 160. Dialog component 160 may include conversational functionality that facilitates discourse between a medical professional and the virtual medical assistant. As discussed above, the virtual medical assistant may be configured to provide one or more responses to a medical professional in connection with free-form instruction received from the medical professional. Dialog component 160 may contribute, in full or in part, to the formulation of such responses based on the content of the free-form instruction, the context of the situation, and/or the intent of the one or more responses to be provided to the medical professional.

Dialog component 160 may be coupled to NLU/CLU component 140 so as to obtain information regarding the content of the free-form instruction (e.g., to receive information regarding one or more identified medical tasks specified in the free-form instruction) to ascertain whether a response to the medical professional is needed and, if so, how the response should be formulated and what information the response should contain. Dialog component 160 may be capable of carrying out different dialogs as appropriate to obtain information needed to complete a plurality of medical tasks. For example, a medical task may have an associated structured representation comprising a plurality of fields corresponding to information regarding the respective medical task that is maintained by dialog component 160 or by a component accessible by dialog component 160. Some fields may correspond to parameters that are required to perform the associated medical task and some fields may correspond to optional parameters.

Dialog component 160 may operate in conjunction with NLU/CLU component 140 to identify one or more medical tasks specified in a medical professional's free-form instruction, and to populate the appropriate fields in the representation associated with the identified medical task(s) either with information extracted by NLU/CLU component 140 from the free-form instruction, information inferred therefrom, inferred from the context or state of the discourse with the medical professional, or inferred from data available from one or more network resources. Dialog component 160 may determine that one or more required fields have not been populated as a result of processing received free-form instruction (e.g., certain information could not be obtained or inferred from the free-form instruction, or otherwise inferred) and, in response, formulate an appropriate response to the medical professional to obtain the missing information. The response may then be provided to the medical professional via the virtual medical assistant application 110 on the host device (e.g., the medical professional's mobile device). Similarly, dialog component 160 may ascertain that certain optional information is missing and deem it appropriate to formulate a response designed to solicit this information from the medical professional. Dialog component 160 may also be configured to formulate a response when the information needed to perform a medical task is complete, for example, to provide a confirmatory response to the medical professional to ensure that the task is the one intended and the parameters ascertained by the virtual medical assistant are correct.

Dialog component 160 may be configured to work in concert with CLU/NLU component 140 to formulate responses designed to solicit information from the medical professional to resolve any ambiguities and/or uncertainty that resulted from processing free-form instruction received from the medical professional. For example, processing performed by CLU/NLU component 140 may have resulted in uncertainty with respect to the medical task the medical professional would like performed or may have resulted in multiple possibilities in this respect. Processing by CLU/NLU component 140 may have resulted in uncertainty regarding one or more parameters associated with the medical task or needed to complete the medical task. Such ambiguity and/or uncertainty may have resulted from an incomplete understanding of the free-form instruction, incomplete or relatively low confidence recognition of the free-form instruction (e.g., when the free-form instruction is received as speech), incomplete or ambiguous instruction from the medical professional, or a combination thereof. CLU/NLU component 140 may convey any ambiguity and/or uncertainty to dialog component 160 to formulate a response designed to resolve any ambiguity/uncertainty or obtain clarification regarding questions or concerns in connection with the free-form instruction.

As discussed above (and as discussed in further detail below), the virtual medical assistant may be configured to process free-form instruction and identify one or more conflicts with respect to the compatibility and/or suitability of performing one or more medical tasks identified from free-form instruction received from the medical professional. For example, problematic interactions between one or any combination of medications, allergies, procedures, conditions, etc., may be identified in the course of processing the free-form instruction. As discussed in further detail below, such conflicts may be identified in part by utilizing one or more medical resources such as EHR system 170, CDS resource 180, medical information retrieval resource 155 or other available resources. Dialog component 160 may be configured to receive information regarding such conflicts and formulate one or more responses to alert the medical professional as to the existence of the conflict and/or to inquire how the medical professional would like to proceed in view of the identified conflict(s).

According to some embodiments, dialog component 160 may assess whether a compound instruction is appropriate under given circumstances. For example, based on the assessment that the medical professional is intending to order a medication, dialog component 160 may determine that it is important to both recite the identified parameters that have been extracted from the free-form instruction (e.g., by NLU/CLU component 140) or inferred therefrom, as well as inquire after one or more missing parameters.

The above described functionality with respect to dialog component 160 is merely exemplary and a given dialog component may implement some portion or all of the functionality described above, or may implement additional functionality not described herein or described in connection with another component or resource. In addition, some of the functionality described in connection with dialog component 160 may be performed, in whole or in part, by other components or resources (including the virtual medical assistant application resident on the host device and/or a virtual medical assistant application server, if implemented), as functionality described above, when and if implemented, can be performed by any suitable component or combination of components.

As discussed above, the system illustrated in FIG. 1 also includes a number of medical resources, including EHR system 170. EHR system 170 may include one or more components that store the electronic medical records for patients of one or more health care institutions. Many healthcare institutions are transitioning or have transitioned from paper documentation to electronic medical record (EMR) systems, in which patients' medical information is stored in a data repository in electronic form. The information that was previously memorialized in paper form as the patient's "chart" may be archived as an electronic health record (EHR) for the patient, along with any other relevant patient data. For example, an EHR for a patient may include any one or combination of the patient's demographic information, intake forms, history, immunization records, laboratory results, medical professional's notes memorializing patient encounters/visits, surgical, pathology and/or radiology reports, diagnostic reports, imaging results or other diagnostic test results, consult notes, discharge summaries, etc.

Thus, an EHR is an electronic medical record that generally is maintained by a specific healthcare institution and contains data documenting the care that a specific patient has received from that institution (or other institutions) over time. EHR system 170 may include electronic medical records for patients from a given institution or from multiple institutions. EHR system 170 may include one or any combination of separate EHR systems, corresponding to respective single or multiple institutions, or may include one or any combination of EHR systems that are integrated or otherwise communicatively coupled. EHR system 170 may also include other functionality in addition to archiving, managing and updating electronic medical records and/or may store other medical information of a more general nature (e.g., not specific to a particular patient), or other information specific to an institution (e.g., standards, standard operating procedures, policies, etc).

Another medical resource illustrated in FIG. 1 includes medical decision support (CDS) service 180. CDS service 180 is a resource for assessing medical conflicts. For example, CDS service 180 may include information about the suitability and compatibility of medications, medical/surgical procedures, and/or diagnostic tests, etc., and interactions therewith. For medications, CDS service 180 may include information regarding dosages, forms and routes of administration, compatibility between different types of medication, compatibility of medications with particular allergies, etc. With respect to procedures, CDS service 180 may include information regarding compatibility between certain procedures and pre-existing medical conditions, compatibility with medications, etc. CDS service 180 may provide other types of information in this regard, as the aspects are not limited in this respect. In some systems, CDS functionality may be provided in whole or in part by EHR system 170, or EHR system 170 may integrate CDS service 180 or be capable of utilizing CDS service 180 as a resource, and the illustrated configuration in FIG. 1 is merely exemplary. It should be appreciated that CDS service 180, if implemented, may include any amount of information including one, some or all of the types of information described above.

Another medical resource illustrated in FIG. 1 includes order fulfillment system 190. Order fulfillment system 190 may include one or more systems capable of fulfilling orders submitted in an applicable electronic format. Order fulfillment system 190 in FIG. 1 denotes any one or combination of available order fulfillment systems or resources capable of fulfilling applicable orderable items. The one or more order fulfillment systems may be a single system or multiple systems and is/are illustrated together for convenience. According to some embodiments, order fulfillment system 190 includes a Computerized Physician Order Entry (CPOE) system capable of receiving and processing electronic orders for one or any combination of medications, laboratory tests, radiology screenings, surgical or other medical procedures and/or other planned treatment action items.

As discussed above, some embodiments include a virtual medical assistant configured to identify instruction to order one or more orderable item specified in free-form instruction, and assist the medical professional in placing the order. In this respect, the virtual medical assistant may be configured to access order fulfillment system 190 to facilitate the dispatch of orders received by the virtual medical assistant from the medical professional. To facilitate electronic ordering, the virtual medical assistant may be configured to utilize any industry standard electronic interfaces to connect with and communicate with order fulfillment system 190, or may use any specialized or proprietary interfaces or formats needed to utilize one or more order fulfillment systems. For example, a virtual medical assistant may generate an order to be presented as an electronic message in accordance with the HL7 standard or in any other suitable manner. Examples of industry standard electronic interfaces include ePrescribing or CPOE for prescriptions, the CPOE system for ordering procedures, and any of numerous systems for ordering lab tests, order management scheduling systems, etc.

The exemplary system illustrated in FIG. 1 also includes medical information retrieval resource 155 that may be utilized by a virtual medical assistant in accordance with some embodiments. Medical information retrieval resource may include one or more resources that are available to provide or procure medical information and may include one or more medical information repositories and/or one or more search facilities configured to respond to queries to locate medical information stored in the one or more medical information repositories. According to some embodiments, a virtual medical assistant may utilize medical information retrieval resource 155 to facilitate responding to medical professional inquiries, to identify one or more conflicts, to infer information needed to perform one or more medical tasks, or for one or more other purposes pursuant to assisting a medical professional. However, a virtual medical assistant need not be configured to access such a medical information retrieval resource 155, as the aspects are not limited in this respect.

As discussed above, the inventors have recognized benefits of a virtual medical assistant configured to assist a medical professional in performing one or more medical tasks that the medical professional may need assistance in performing including, but not limited to, any one or combination of accessing patient information, preparing and/or submitting an order for an orderable item (e.g., preparing and/or submitting a medication order, a procedure order, a lab order, a diagnostic test order, an appointment order, a referral order, a consultation order, etc.), capturing, evaluating and/or archiving dictation associated with a patient encounter, scheduling appointments, etc. The virtual medical assistant may be configured to interact with the medical professional in real-time to assist in the completion of medical tasks desired by the medical professional. Such interactivity allows for the virtual medical assistant to respond to instructions received from the medical professional to obtain missing information, disambiguate instruction, identify desired medical tasks, identify conflicts and alert or warn the medical professional regarding the conflicts, confirm an understanding of instructions received, etc. Additionally, interaction with the medical professional may allow the virtual medical assistant to infer information needed to perform one or more medical tasks, for example, using information in previously received instruction, information obtained in performing one or more medical tasks in response to previously received instruction, information in electronic medical records and/or medical information accessed over a network. Some exemplary techniques with respect to implementing a virtual medical assistant according to some embodiments are described in further detail below.

Figure 2:
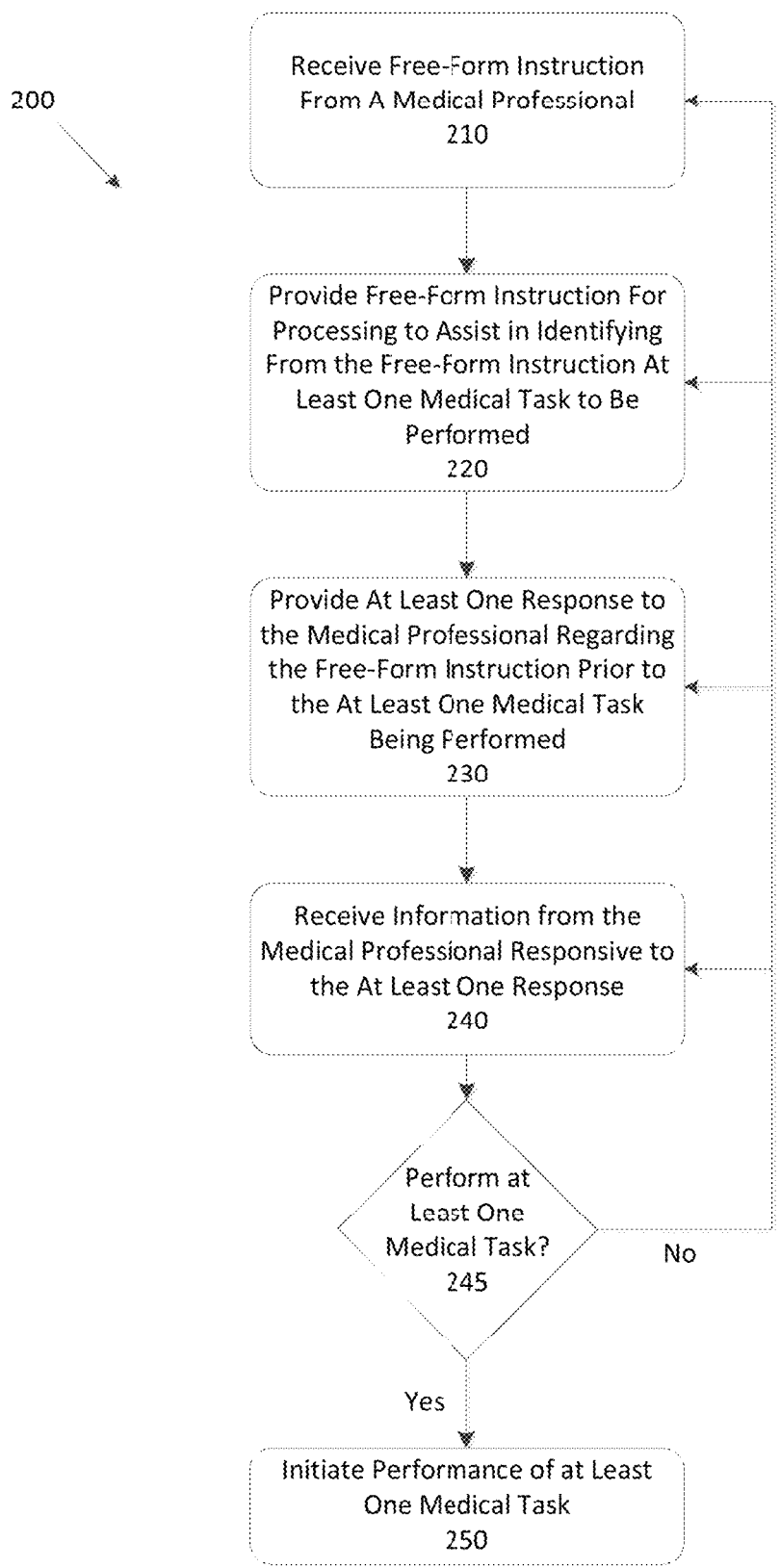
FIG. 2 illustrates a method of interacting with a medical professional to assist with one or more medical tasks specified in free-form instruction from the medical professional, in accordance with some embodiments.

FIG. 2 is a flow chart illustrating a method performable by a virtual medical assistant to assist a medical professional, wherein the virtual medical assistant is implemented, at least in part, by at least one processor of a host device, according to some embodiments. The host device may be a mobile device, for example, the medical professional's smart phone having a virtual medical assistant application installed as an application or "app" on the smart phone, or may be any other suitable device capable of hosting a portion of a virtual medical assistant (e.g., a virtual medical assistant application). The host device may include one or more wireless transceivers capable of communicating with at least one network and/or external device so that the virtual medical assistant application can access one or more network resources for which the virtual medical assistant application is configured to cooperate with.

In act 210, free-form instruction is received by the virtual medical assistant from the medical professional (e.g., via interface functionality on a mobile device or other interface device). For example, the medical professional may speak the free-form instruction and the virtual medical assistant application may receive the free-form speech instruction via one or more microphones coupled to the mobile device. Alternatively, the free form instruction may be received via another input component (e.g., via one or more other input mechanisms coupled to a mobile device). For example, the medical professional may type the free form instruction via a key pad or touch sensitive display screen on a mobile device and the virtual medical assistant application may receive the free-form instruction as a free-form textual instruction. The free-form instruction may be received in any other suitable way, as the aspects are not limited in this respect (e.g., free-form instruction may be received via an interface component separate from the host device on which the virtual medical assistant application is at least partially implemented).

In act 220, the received free-form instruction is provided by the virtual medical assistant application for processing to identify one or more medical tasks specified in the free-form instruction by the medical professional. According to some embodiments, after performing pre-processing of the free-form instruction (if any such pre-processing is needed or desirable), the virtual medical assistant application may transmit the free-form instruction to be processed by one or more resources connected to a network accessible by the host device. For example, the virtual medical assistant application may provide the free-form instruction to a medical understanding resource to analyze the free-form instruction to determine its content and meaning, for example, by utilizing an ASR component, NLU/CLU component and/or a dialog component to process the free-form speech to identify a medical task and/or one or more parameters associated with the identified medical task. According to some embodiments, other network resources are utilized to assist in identifying one or more medical tasks specified in the received free-form instruction.

In some instances, processing the free-form instructions results in identification of one or more impediments to performing the identified at least one medical task. The term "impediment" refers herein to any condition that generally impedes, complicates and/or otherwise gives rise to questions or concerns with respect to performing at least one identified medical task. Examples of impediments are missing information needed (or optionally used) to perform at least one medical task or an aspect of at least one medical task, ambiguity with respect to performing at least one medical task, conflicts associated with at least one medical task, uncertainty as to the nature of one or more specified medical tasks, etc. As should be appreciated from the examples given above, an impediment need not operate to absolutely prevent or bar the at least one medical task from being performed, but need only give rise to a question or concern in this respect (e.g., a free-form instruction may include sufficient information to complete the order, but a compatibility or suitability conflict may have been identified). However, some impediments may indeed prevent performance of the identified medical task (e.g., missing information required to complete an order for an orderable item may be identified). It should be appreciated that in some instances multiple impediments may be identified and in other instances no impediments may be identified.

In act 230, at least one first response is provided to the medical professional by the virtual medical assistant by, for example, the virtual medical assistant application presenting the at least one first response to the medical professional via the host device (e.g., a mobile device) prior to the at least one identified medical task being performed (or by presenting the at least one first response via any interface device utilized by the medical professional). For example, the at least one first response may be displayed to the medical professional on a display of a mobile device and/or the at least one first response may be presented as audio to the medical professional using speech synthesis techniques and rendering the speech via one or more speakers coupled to the mobile device. According to some embodiments, the at least one first response may be both visually and audibly rendered to the medical professional, or a single mode of presentation may be used, as the aspects are limited for use with any particular presentation or rendering technique.

The one or more techniques for rendering information to the medical professional may depend on the interface device utilized by the medical professional and/or the environment of the medical professional. For example, the display capabilities of a mobile device may be limited in which case an audio presentation may be preferable, or the medical professional may be utilizing the virtual medical assistant in an environment where the focus of the medical professional is trained elsewhere (e.g., while driving, while performing an examination or procedure, etc.) such that an audio presentation may be preferred (with or without a corresponding visual rendering of the at least one first response). According to some embodiments, the interface utilized by the medical professional may include only voice capabilities such that interaction between the medical professional and the virtual medical assistant is conducted audibly. In some circumstances, the medical professional may be using the virtual medical assistant in circumstances where audio presentation may be inappropriate or difficult to hear or understand, such that a visual rendering of the at least one response alone may be preferable. However, responses from the virtual medical assistant may be provided and rendered in any suitable way, format or mode, as the aspects are not limited in this respect.

The at least one first response, however presented, may be any response deemed appropriate by the virtual medical assistant in connection with the identified at least one medical task. For example, the virtual medical assistant may identify one or more impediments to performing the at least one medical task and formulate (e.g., using a dialog component) the at least one first response to include one or more inquiries provided to the medical professional with respect to the one or more identified impediments. In this respect, the at least one first response may be formulated to include a request that the medical professional provide at least some missing information needed to perform at least one medical task or an aspect of at least one medical task, a request for information to assist in resolving one or more ambiguities associated with performing at least one medical task, a question about what type of medical task the medical professional would like performed, one or more alerts, warnings and/or cautions associated with at least one identified medical task, etc.

The at least one first response alternatively may be unrelated to any impediment. For example, the virtual medical assistant may identify one or more medical tasks without detecting any impediment to performing the at least one medical task, but nevertheless, the medical virtual assistant may want to request confirmation from the medical professional before initiating performance of the identified medical task. Thus, the at least one first response may be formulated to include a statement regarding an understanding of the free-form instruction and/or a recitation of the at least one medical task that the virtual medical assistant intends to initiate performance of and/or any details that are relevant (e.g., one or more parameters associated with the task). The at least one first response may be formulated to include a request that the medical professional confirm that the understanding is correct and/or a request for confirmation to proceed with performance of an identified medical task.

In act 240, the virtual medical assistant receives information from the medical professional responsive to the at least one first response. For example, the medical professional may respond by providing missing information, disambiguation information, guidance with respect to at least one medical task, confirmation to proceed, verification as to the understanding of the free-form instruction, cancellation of the free-form instruction, modification to the free-form instruction, etc. The information from the medical professional may be received by the virtual medical assistant application via any suitable interface device (e.g., using a mobile device) using any of the input mechanisms described above in connection with receiving free-form instruction.

In act 245, the virtual medical assistant may assess whether the at least one medical task should be performed based, at least in part, on the information received from the medical professional. In particular, the virtual medical assistant may evaluate the information to assess whether the at least one medical task should be performed. For example, the virtual medical assistant system may check to see if all of the information needed to perform a requested medical task has been obtained, or whether further information is needed, whether ambiguities are resolved or further clarification is required, whether the medical task to be performed has been correctly identified, whether any conflicts have been cleared or the instruction modified to remove the conflict, whether the medical professional has confirmed that a requested medical task should be performed, etc. If one or more impediments have been sufficiently overcome and/or the medical professional has confirmed the understanding of the free-form instruction and authorized the virtual medical assistant to proceed, the virtual medical assistant may initiate performance of at least on medical task identified in the free-form instruction (act 250).

If the virtual medical assistant deems that further information is needed to perform an identified medical task, any one or combination of acts 210-240 may be again performed. For example, the virtual medical assistant may return and await further free-form instruction from the medical professional (e.g., in the event the medical professional decided to not proceed with an identified medical task). Alternately, the virtual medical assistant system may again process the free-form instruction in view of the further information and/or one or more further responses may be generated and provided to the medical professional by the virtual medical assistant to invoke the medical professional to provide further information regarding the free-form instruction. The virtual medical assistant system may also assess whether further information may now be inferred based on the additional information received from the medical professional.

It should be appreciated that this type of dialog between the medical professional and the virtual medical assistant may continue until it is determined that one or more medical tasks are ready to be performed and/or authorized by the medical professional. In this manner, the virtual medical assistant may interact with the medical professional in real-time to assist the medical professional in performing medical tasks and/or in performing medical tasks on behalf of the medical professional. It should be further appreciated that identifying at least one medical task and interacting with the medical professional may include other acts not explicitly described in connection with the method illustrated in FIG. 2. Furthermore, no one or any particular combination of acts are required to be performed, nor do acts need be performed in the order described in connection with FIG. 2, or in any particular order, as the aspects are not limited in this respect. Instead, method 200 merely provides an example of an interaction between a medical professional and a virtual medical assistant system according to some embodiments.

As one example of performing method 200, a medical professional may provide the following free-form instruction in connection with a patient planning an ascent of Mount Kilimanjaro with a night stay in the crater: "Start John Doe on Diamox, 250 mg pills taken once daily beginning two days prior to ascent." The virtual medical assistant may process the free-form instruction and recognize that Diamox is the brand name for the active ingredient acetazolamide. The virtual medical assistant may access John Doe's patient records and determine that the patient is allergic to sulpha-based drugs. In response, the virtual medical assistant may formulate a response including an alert to the medical professional to this detected drug-allergy interaction by providing the following response: "Patient John Doe is allergic to sulpha-based drugs. Do you want to continue?" In response, the medical professional may decide to change the prescription by providing the following instruction: "Okay, order Dexamethasone instead."

The virtual medical assistant may receive the further instruction from the medical professional, process the instruction to ascertain that the medical professional has changed the prescription to the steroid Dexamethasone. In processing the further free-form instruction, the virtual medical assistant may ascertain that the medical professional has failed to provide a number of details needed to complete and dispatch the medication order (e.g., dose, frequency, route, etc.). The virtual medical assistant may provide a response to the medical professional as follows: "Change medication order for patient John Doe to Dexamethasone. To complete this order, please provide prescription details." The medical professional may respond with the instruction "4 mg pills taken orally twice a day starting the day before ascent." This example discourse may continue until the virtual medical assistant has obtained the information needed to complete and dispatch the medication order, including, according to some embodiments, a recitation of the completed order and a request for the medical professional to confirm the order and/or for the medical professional to provide any needed verification information.

As one example of performing method 200 wherein the virtual medical assistant requests further guidance regarding the medical task(s) to be performed, a medical professional may provide the following free-form instruction: "I need to consult with Dr. Jones to discuss an ultrasound guided biopsy for kidney mass and surrounding lymph nodes." The virtual medical assistant may receive this free-form instruction, process the instruction and determine that clarification on the intended directives of the medical professional is needed. For example, the virtual medical assistant may want clarification as to whether the medical professional wants to schedule a consultation with Dr. Jones, order the biopsy procedure, or both. In response, the virtual medical assistant may provide a response to the medical professional as follows: "Would you like me to schedule a consultation with Dr. Jones?" If the medical professional responds in the positive, the virtual medical assistant can initiate processes to set-up the consultation. The virtual medical assistant, having identified multiple potential tasks to be performed, may follow-up with the inquiry: "Would you like me to order the ultrasound biopsy for kidney mass and surrounding lymph nodes?" to which the medical professional may reply: "No, let's wait until after the consultation." The virtual medical assistant may note the date and time of the scheduled consultation and set up an internal reminder to follow-up after the consultation has taken place. After the consultation has occurred, the reminder set by the virtual medical assistant may trigger the virtual medical assistant to provide the following inquiry to the medical professional "Would you like to order the ultrasound guided biopsy of the kidney mass and surrounding lymph nodes pursuant to your consultation with Dr. Jones?" In this way, the virtual medical assistant can proactively assist the medical professional in his/her practice.

As an example of performing method 200 wherein the at least one response is not related to an impediment, a medical professional may provide the following free-form instruction to the medical professional: "Set up a full blood panel for Jane, with RBC and WBC count and urine test." The virtual medical assistant may receive and process the free-form instruction and ascertain that the medical professional would like to order lab tests for Jane Doe and may respond with the following: "Laboratory test for patient Jane Doe: Full blood panel including red blood cell and white blood cell count and urine test. Any special instructions?" The medical professional may respond with the following: "Yes, 12-hour fast required." The above exemplary interaction may facilitate the provision of a comprehensive order for a lab test for the patient. According to some embodiments, the virtual medical assistant may follow-up the above dialog to provide an additional response that recites the order that the assistant intends to place (including the special instructions received) and request that the medical professional confirm the order.

It should be appreciated that the above exemplary dialogs between the medical professional and a virtual medical assistant are merely exemplary of the types of discourse that a virtual medical assistant may implement in assisting a medical professional. Any suitable exchange between a medical professional and a virtual medical assistant may be performed to assist a medical professional in performing one or more medical tasks, as the aspects are not limited to any particular type or form of interaction. Some further examples are described below for illustration.

Method 200 described above in connection with FIG. 2 illustrates certain discourse capability of a virtual medical assistant system that allows the virtual medical assistant to interact with the medical professional to probe, inquire, question, request, confirm and/or verify in connection with free-form instruction received from the medical professional. According to some embodiments, a virtual medical assistant system may be implemented that can infer information in connection with free-form instruction provided by a medical professional. In this manner, the virtual medical assistant may be able to handle and act upon free-form instruction that may be incomplete, ambiguous, inconsistent and/or that gives rise to one or more conflicts in connection with one or more medical tasks specified in received free-from instruction.

Figure 3:
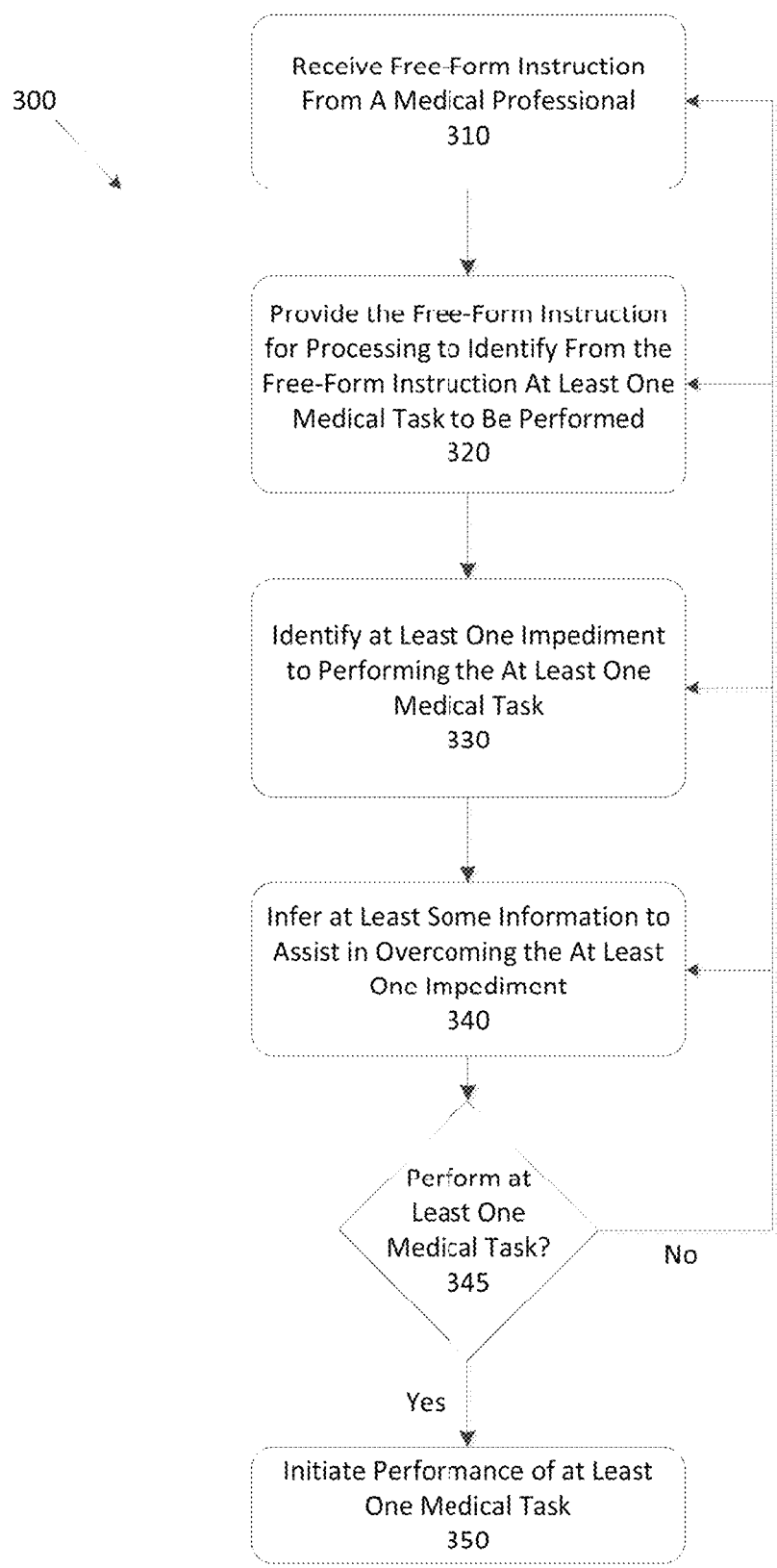
FIG. 3 illustrates a method of inferring information in connection with at least one medical task specified in free-form instruction from the medical professional, in accordance with some embodiments.

FIG. 3 includes a flow chart illustrating a method that may be performed by a virtual medical assistant to assist a medical professional by inferring at least some information in connection with free-form instruction received from the medical professional. Acts 310 and 320 may be similar in some respects to acts 210 and 220 described above in connection with method 200 illustrated in FIG. 2 in that free-form instruction may be received from a medical professional by the virtual medical assistant and processed to identify at least one medical task to be performed. For example, free-form instruction may be received from the medical professional via a host device on which a virtual medical assistant application is operating (or via other interface component(s)), and the free-form instruction may be transmitted over a network to be processed by one or more components forming, at least in part, the virtual medical assistant to identify any medical tasks specified in the free-form instruction.

In act 330, at least one impediment to performing a medical task ascertained from the free-form instruction is identified. For example, the virtual medical assistant may process the free-form speech (e.g., using a medical understanding resource) to understand the content of the free-form speech to ascertain what the medical professional is instructing the virtual medical assistant to do or assist with. In doing so, one or more impediments to carrying out the directives of the medical professional may be identified. For example, the virtual medical assistant may determine that information needed to perform a requested medical task is missing, may identify one or more ambiguities in the medical professional's instruction, or may otherwise detect one or more conditions that impede, complicate and/or raise uncertainty with respect to performing one or more identified medical tasks.

In act 340, at least some information is inferred to assist in overcoming the identified at least one impediment. For example, the virtual medical assistant may infer information based on information available to one or more components of the virtual medical assistant, or available via one or more network resources accessible by the virtual medical assistant. According to some embodiments, the virtual medical assistant evaluates previously received instruction from the medical professional and/or information obtained responsive to previously received instruction to infer the at least some information.

To illustrate an example of inferring at least some information regarding one or more impediments to performing a medical task, a medical professional may have provided the virtual medical assistant the instruction: "Show me John Doe's chart." In response to the instruction, the virtual medical assistant may have initiated processes to obtain John Doe's patient history or other relevant records from, for example, an EHR system accessible by the virtual medical assistant, and presented at least a portion of John Doe's "chart" to the medical professional. In response or subsequent to receiving patient information for John Doe, the medical professional may speak the free-form instruction "Please refill prescription." The virtual medical assistant may process the instruction and identify that the medical professional would like to order a medication, but also ascertain that there is information missing that is needed to perform the requested medical task. In particular, the patient name is not explicit in the instruction, and the medication, dose, frequency, administration, quantity, etc. are missing entirely.

The virtual medical assistant may infer one or more of these missing parameters from previous instruction or information obtained from performing tasks responsive to previous instructions. For example, the virtual medical assistant may recognize that the medical professional is likely referring to John Doe due to the previous instruction to "Show me John Doe's chart." In addition, the virtual medical assistant may understand that the medical professional is ordering a refill on a prescription and that the prescription information may be present in the patient history obtained in response to the instruction to obtain John Doe's chart, or otherwise obtainable from an EHR system storing records for John Doe. Accordingly, the virtual medical assistant may infer at least some of this information from the electronic medical record for John Doe.

In the example above, in attempting to infer at least some information in connection with the prescription that the medical professional intends to fill, the virtual medical assistant may discover from John Doe's EMR that John Doe has multiple medication prescriptions. The virtual medical system may provide a response to the medical professional to obtain clarification (e.g., the virtual medical assistant may perform functionality similar to or the same as act 230 in method 200 illustrated in FIG. 2). For example, the virtual medical assistant may present to the medical professional the multiple prescriptions that were located (or an identifying shorthand such as the medication name) along with a visual and/or audible response such as "John Doe has multiple prescriptions. Please select the prescription you would like to refill." The medical professional may then identify the desired prescription to allow the virtual medical assistant to proceed with the medication order. Otherwise, if John Doe has only a single prescription, the virtual medical assistant may infer that this is the prescription the medical professional intends to refill and obtain the needed information from John Doe's electronic medical record.

Prior to performing the medical task of ordering the medication, the virtual medical system may present its understanding of the instruction and the details of the prescription refill (e.g., the parameters of the medication order) to the medical professional to confirm that the instruction was understood correctly and to confirm that any inferred information is correct. In the above example, the virtual medical assistant may present to the medical professional the confirmation "Medication order for patient John Doe, Albuterol inhaler to be taken by oral inhalation as needed. Please confirm medication order." If the medical professional confirms (e.g., act 345 results in a yes), the virtual medical assistant may initiate processes to submit the medication order, such as generating a complete medication order and submitting it to a CPOE system.

The virtual medical assistant may also infer one or more parameters based on medical knowledge obtained from one or more medical information resources available to the virtual medical assistant (e.g., via one or more information retrieval resources). For example, the medical professional may say "Start John Doe on Compazine 2-3 times daily as needed for nausea." While the medical professional does not explicitly state that the medication should be taken orally, the virtual medical assistant may infer oral administration by ascertaining that Compazine is the brand name for the oral form of the drug prochlorperazine. In responding to the medical professional (e.g., in a confirmatory response or, for example, to inquire as to the dose), the virtual medical assistant may include this inference in its recitation of the medication order provided to the medical professional (e.g., "Medication order for patient John Doe. Oral administration of Compazine in pill form 2-3 times a day as needed for nausea. What dose of the prochlorperazine should be administered?").

As a further example, free-form instruction may mention an "IV," (i.e., the medical route intravenous), and the virtual medical assistant may infer that the medication should be administered in a liquid form (which may be a parameter needed to complete an order for a medication) so that in some embodiments described herein, the liquid form can be included in the order for the medication because it is implied. As another example, if the free-form instruction indicates that medication should be administered "stat," the virtual medical assistant may infer that the medication needs to be administered immediately, which may enable the virtual medical assistant to populate the start time field in an order form for the medication.

The virtual medical assistant may also infer information based on its knowledge of the medical professional and/or the medical professional's practice. For example, the medical professional may say "Jane Doe needs a CT scan of chest and neck, with co." The virtual medical assistant may receive the free-form instruction, process the free-form instruction to ascertain that the medical professional would like to order a diagnostic test. While the medical professional does not specify a radiology site to perform the diagnostic test, the virtual medical assistant may infer the radiology site based on the medical professional's primary affiliation with an institution, previous indication of a site to perform radiology tests, or other information available to the virtual medical assistant that would suggest one site over another. The virtual medical assistant may present its inference to the medical professional in a confirmatory response or in a response to obtain any further information needed to complete and dispatch the order for the diagnostic test.

Method 300 described above in connection with FIG. 3 illustrates certain inference capabilities of a virtual medical assistant system according to some embodiments that allow the virtual medical assistant to perform medical tasks, conduct actions on behalf of or otherwise assist a medical professional in circumstances where medical professional instruction is incomplete, ambiguous or otherwise gives rise to questions, by inferring at least some information about the one or more medical tasks to be performed. As examples above illustrate, techniques for inferring information may be used alone or in combination with techniques for interacting with the medical professional through discourse (e.g. providing responses to the medical professional in connection with received free-form instruction) to provide a system that may allow a medical professional to conduct his/her practice more efficiently, conveniently and/or safely, though achieving such benefits is not a requirement of techniques described herein, or of any implementation.

As discussed above, according to some embodiments, a virtual medical assistant may be configured to perform one or more tasks that may assist in a medical professional's practice of medicine. Exemplary tasks include, but are not limited to, sending messages (text, email, voice, etc.), scheduling meetings, capturing and/or processing medical dictation, accessing medical information in EMRs and/or locating and presenting information from and EHR system, preparing and submitting orders (e.g., medication orders, lab orders, procedure orders, diagnostic test orders, consultation orders, referral orders, etc.), providing medical decision support through medical search and alerts, etc. It should be appreciated that a virtual medical assistant may implement one or any combination of the above exemplary tasks, or others not explicitly described herein, and there are no requirement that a virtual medical assistant perform any particular task.

According to some embodiments, a virtual medical assistant can operate as an interface to an EHR system to access EMRs to obtain patient information requested by the medical professional and/or to assist in the performance of medical tasks requested by the medical professional. The virtual medical assistant may maintain patient context across multiple instructions from the medical professional to facilitate a meaningful presentation to the medical professional and to allow the virtual medical assistant to infer information in connection with medical professional instruction.

In this respect, the virtual medical assistant may operate as an EMR portal to retrieve patient information for review by the medical professional and/or to assist in performing one or more medical tasks including, but not limited to, any one or combination of obtaining and presenting a list of current patients, selecting a patient for more detailed viewing, searching for patients that match specified criteria and obtaining information on selected patients. For selected patients, more detailed information may be obtained via the virtual medical assistant. For example, the virtual medical assistant may present a patient chart (or portion thereof) or other patient data from the associated EMRs such as current problem or disorder list, current medication list, allergy list, current order, patient history notes such as medical notes, consult notes, operative reports, surgical, pathology, radiology reports, progress notes, treatment summaries, discharge summaries, diagnostic test results, imaging results, etc. In this respect, the virtual medical assistant may be configured to navigate a given EHR system and individual EMRs to obtain patient information requested by the medical professional.

As discussed above, some embodiments include a virtual medical assistant configured to assist a medical professional in electronically ordering an orderable item. For example, the virtual medical assistant may receive free-form instruction from the medical professional that includes instruction to place an order, and may process the free-form instruction to prepare, complete and/or dispatch the order, which may include making one or more inferences about the order or orderable item and/or interacting with the medical professional to obtain further information in this regard. The virtual medical assistant may be configured to interface with an order fulfillment system to dispatch the order once the order is complete.

According to some embodiments, a virtual medical assistant may be configured to understand multiple types of orders for any one or combination of orderable items including in-patient orders for medication in a medical facility (e.g., a hospital) and out-patient medication orders (e.g., prescriptions), orders for medical procedures (e.g., an MRI, a CT scan or any of numerous other types of procedures), orders for laboratory work or other tests, referral orders to other medical professionals (e.g., other physicians or specialists, physical therapy, etc.), communication orders (e.g., orders for instructions, counseling, guidance or training for any of numerous topics such as smoking cessation or dietary counseling), etc.

As discussed above, in accordance with some embodiments described herein, a virtual medical assistant may process free-form instruction received from a medical professional using a medical understanding resource that includes an NLU/CLU component to identify the order specified in the free-form instruction. The NLU/CLU component may identify one or more parameters in the order, or may identify information that may be used as a basis for determining or obtaining parameters in the order. The medical understanding resource (e.g., a dialog component used by the medical understanding resource) may have an understanding of the parameters that need to be specified to generate an order of the applicable type. For example, the medical understanding component (or other portion of the virtual medical assistant) may maintain a representation of each order type with which the virtual medical assistant is configured to assist that includes a field for each parameter required and/or optional in a connection with placing the corresponding order.

If the free-form instruction does not fully specify all of the parameters for an order of the orderable item, in accordance with some embodiments, missing parameters can be inferred by the virtual medical assistant using information from previous instructions, or information from resources available to the virtual medical assistant, and/or obtained through dialog with the medical professional. Exemplary parameters for ordering a medication may include the name of the medication (e.g., a commercial medication or drug name or a generic name), a dose, a route, a frequency, a duration and an indication (e.g., specifying a symptom, condition, disease, etc. that indicates that the medication should be taken). Exemplary parameters for a procedure may include an identification of the type of the procedure, as well as a location and date for the procedure. Exemplary parameters for a laboratory procedure or test may include an identification of the type of procedure or test, a date, a frequency if it is to be repeated, and any special instructions regarding the laboratory procedure or test. Exemplary parameters for ordering instructions, counseling, guidance, training, etc. may vary depending upon the nature of the communication order and whether it is to be given verbally or via some reference materials (e.g., written leaflets or other material to be provided to the patient). Parameters for a follow-up visit may include information identifying the type of visit (e.g., is it a special purpose visit to address something in particular, a general check-up, etc.), a date and any special instructions.

When an order is complete, a virtual medical assistant may generate an order and dispatch the order for electronic fulfillment. As discussed above, a virtual medical assistant may interface with a CPOE or other order fulfillment system to automatically place orders for prescriptions, laboratory tests, radiology screenings, surgical or other medical procedures and/or other planned treatment action items, based on processing free-form instruction to obtain parameters needed to complete the order. In accordance with some embodiments, the virtual medical assistant may employ one or more coding systems to facilitate placing an order in its proper form. Such systems can be used to normalize terminology and/or provide one or more codes for an orderable item that may be required by a particular order fulfillment system. For example, a medication with a name "X" may be orderable in a particular order fulfillment system only by using a different name or code "Z". A coding system may use one or more coding standards (e.g., RxNorm for medications, LOINC for laboratory and diagnostic orders, etc.), and the virtual medical assistant may be configured to utilize such systems to place an order in the correct form prior to dispatching the order to the appropriate order fulfillment system.

As discussed above, in accordance with some embodiments, a virtual medical assistant may perform analysis on free-form instruction received from a medical professional to detect and provide an alert for potential conflicts in connection with the order. This can be performed in any suitable manner, some examples of which were discussed above. For example, when the orderable item is a medication, the dosage may be checked by the virtual medical assistant to determine if it is between a minimum and maximum range, and/or its form and route may be checked for consistency. As an another example, recent laboratory results for the patient may be checked to ensure that the medication is compatible with them (e.g., the patient's cholesterol level). As another example, drug interactions may be checked to ensure that the medication being ordered is compatible with medications on the patient's current medication list (drug-drug interaction). As yet another example, a check may be made for a medication to ensure that it is compatible with any allergies in the patient's medical history (drug-allergy interaction). As another example, drug interactions may be checked to assess whether a particular drug is safe for use in connection with a medical condition (drug-condition interaction).

When the orderable item is a procedure, the virtual medical assistant may check to see if the procedure is compatible with any medication taken by the patient (procedure-drug interaction), whether the procedure is safe for a patient with a given condition (procedure-condition interaction), or may detect any other conflicts or issues in connection with a specified procedure and a given patient. It should be appreciated that conflicts with respect to compatibility and/or suitability may be determined by a virtual medical assistant in connection with any one or combination of order types understandable by the virtual medical assistant, as the aspects are not limited in this respect. The virtual medical assistant can perform such determinations in any suitable manner, including using one or more CDS systems that include information about the suitability and compatibility of dosages, forms and routes of medication, compatibility between different types of medication, compatibility of medications with particular allergies, etc.

Described below are a number of example interactions between a medical professional and a virtual medical assistant via a mobile device to illustrate various concepts and techniques related to virtual medical assistance, according to some embodiments. The examples are described in connection with the wireframes in FIGS. 4A-4H which schematically illustrate a virtual medical assistant application installed on a mobile device 401. FIGS. 4A-4H show an exemplary GUI 410 presented to a medical professional by the virtual medical assistant application on a display of mobile device 401 to allow the medical professional to utilize virtual medical assistant functionality, some examples of which are described below in connection with FIGS. 4A-4H.

Figure 4B:
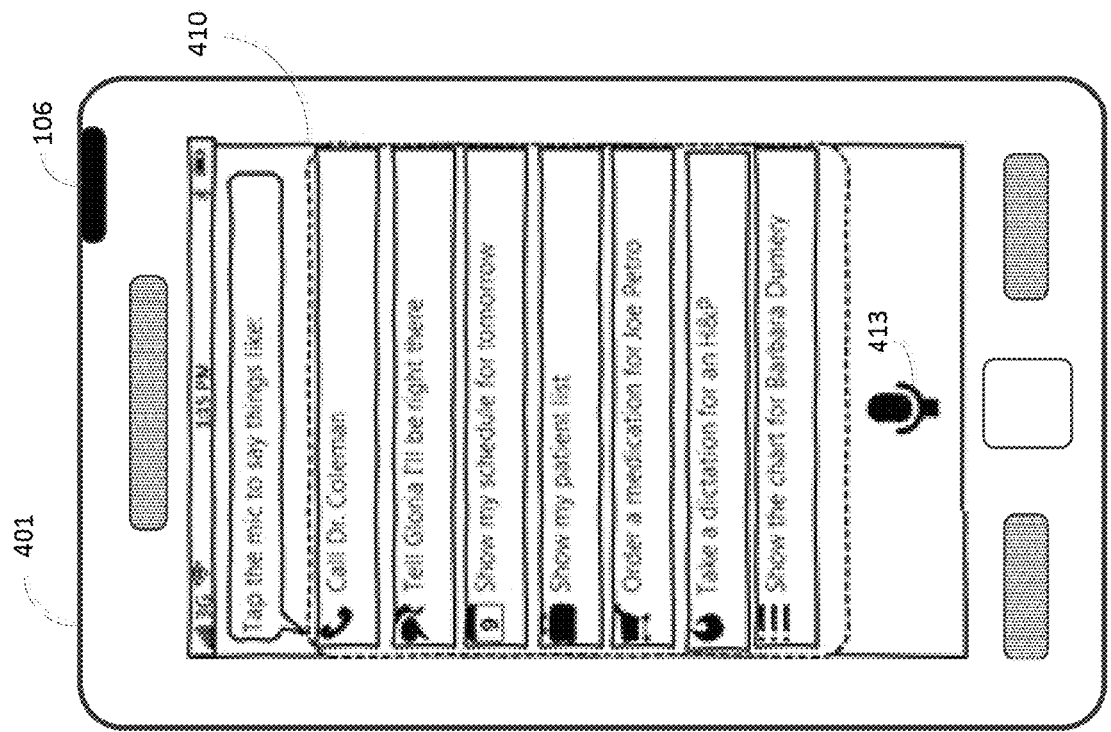
Figure 4A:
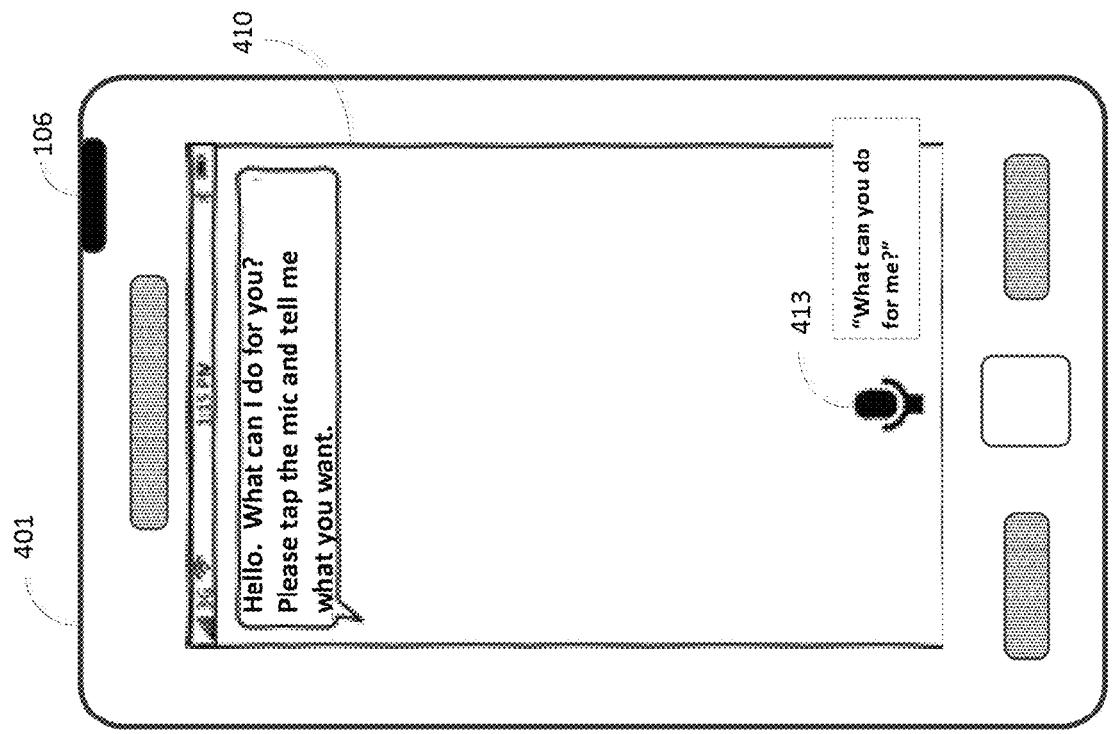

FIG. 4A illustrates GUI 410 presented by a virtual medical assistant on a mobile device, in accordance with some embodiments. The general GUI functionality allows for a tap and speak discourse rendered in a chat-like presentation on mobile device 401. In particular, dialog from the virtual medical assistant and from the medical professional are displayed in dialog icons on a display of mobile device 401. A microphone icon 413 is also presented on the display that the medical professional can tap when the medical professional would like to speak an instruction, which the medical professional can speak in free-form. Spoken free-form instruction is captured by the mobile device and received by the virtual medical assistant application resident on the mobile device. The received free-form instruction may then be processed by the virtual medical assistant by, for example, providing the received free-form instruction to one or more network resources via wireless communication component 406.

FIG. 4A illustrates an exemplary introductory presentation, for example, that may be presented when the medical professional activates the virtual medical assistant (e.g., by launching the virtual medical assistant application on the mobile device). In this example, the virtual medical assistant application displays dialog (and may also audibly render the dialog) indicating that virtual medical assistant is ready to assist and provides guidance to the medical professional by inviting the medical professional to tap the microphone icon and tell the virtual medical assistant what the medical professional would like done. Initially, a medical professional may be unfamiliar with functionality provided by the virtual medical assistant and the virtual medical assistant application may be present a menu of exemplary tasks that the virtual medical assistant can assist the medical professional with or perform on behalf of the medical professional. To this end, the medical professional may say "What can you do for me?" and in response the virtual medical assistant application may present a number of example tasks the virtual medical assistant can perform by providing representative free-form instruction suitable to instruct the virtual medical assistant to perform the associated task, or begin the process of performing such a task. It should be appreciated that the medical professional is not limited to speaking the same words presented in the examples, as the virtual medical assistant may be configured to handle free-form instruction. The menu of examples is intended to give the medical professional a flavor for how to interact with the virtual medical assistant.

The exemplary tasks presented to the medical professional are illustrated in FIG. 4B and include making a telephone call to someone in the medical professional's telephone directory, sending a message (e.g., a text or email) to a designated recipient, requesting that the virtual medical assistant show the medical professional's schedule, patient list or chart for a particular patient, ordering a medication, taking dictation (e.g., to memorialize the results of a patient encounter), etc. A given virtual medical assistant may choose to present any set of possible tasks that the virtual medical assistant can help with, or such "help" functionality may not be implemented at all, as this feature is used to illustrate possible functionality of a virtual medical assistant.

FIG. 4C illustrates the results of the medical professional requesting that the virtual medical assistant "show my patient list." In particular, in response to the medical professional's free-form instruction, the virtual medical assistant presents a list of the medical professional's patients, which may be obtained from a EHR system or other location that maintains this information. As discussed above, a virtual medical assistant may receive instructions from the medical professional in other ways besides speech. FIG. 4D illustrates the result of the virtual medical assistant responding to the medical professional selecting a patient from the patient list, for example, via touch capabilities of the display. In particular, the virtual medical assistant application may interpret the medical professional touching the display on the entry for a particular patient as instruction to retrieve the chart for this patient, which the virtual medical assistant may obtain by accessing an EHR system. It should be appreciated that the medical professional could have provided this instruction using other input mechanism such as, for example, by providing free-form instruction by saying "show me [patient name's] chart," or by typing such an instruction via keypad.

Medical professionals often have busy schedules and may need assistance in scheduling appointments and/or may need reminders to perform certain tasks. An on-the-go medical professional may remember a task that needs to be completed, such as following up with a patient or medical staff in connection with a patient, but may not at a given moment have the time to follow-up, or it may not make logistic sense to do so at a given time. The medical professional may utilize the virtual medical assistant to help manage their busy schedules by assisting in scheduling appointments or patient visits, setting up alerts and/or reminders, managing conflicts on the calendar, etc.

Figure 4F:
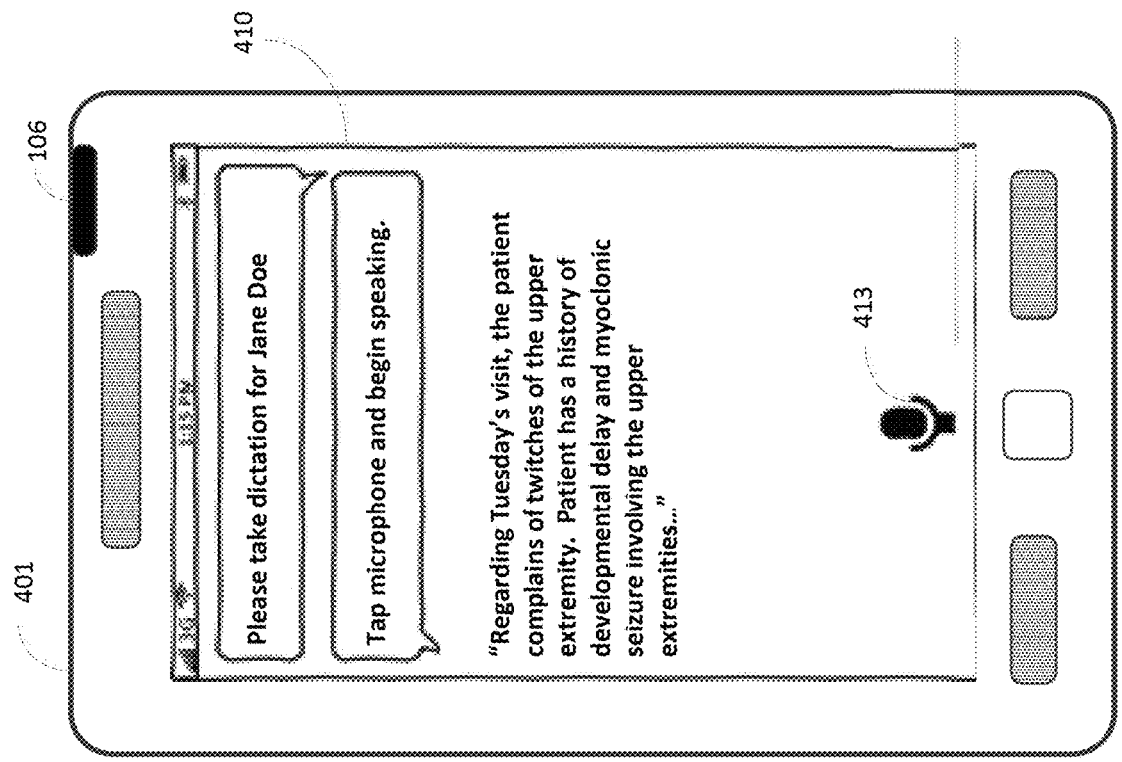
Figure 4E:
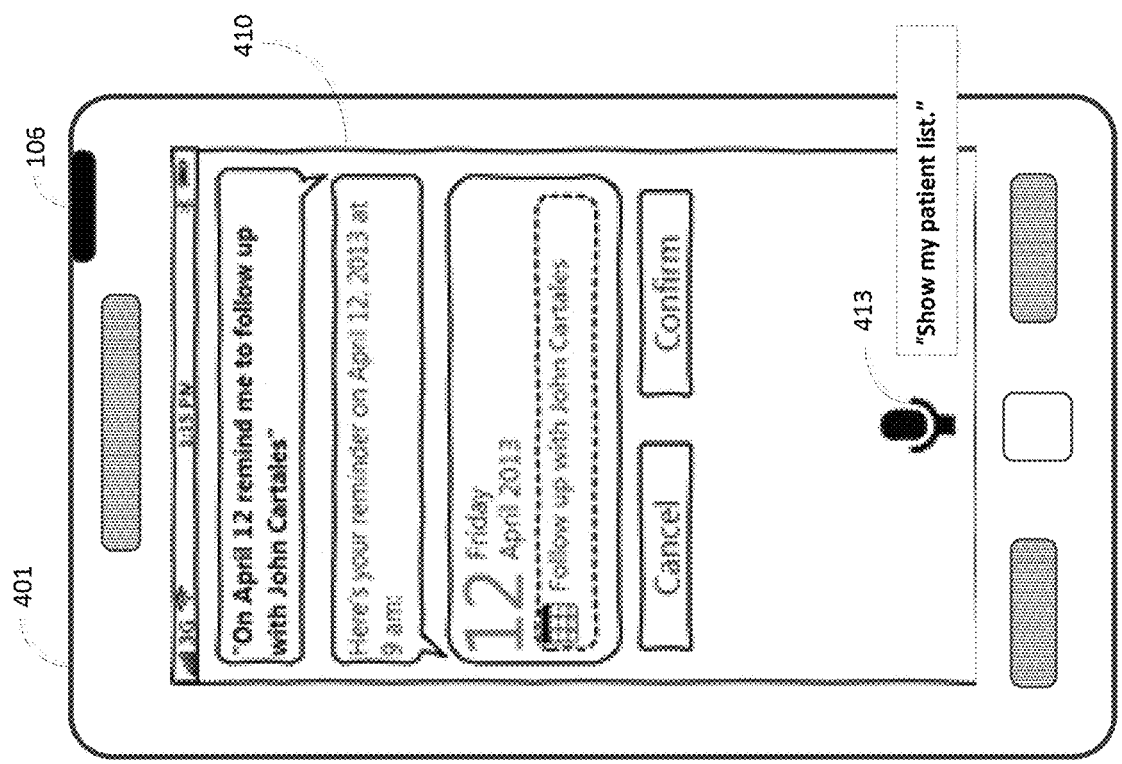

FIG. 4E illustrates a virtual medical assistant helping a medical professional set-up a reminder. In particular, in the example shown in FIG. 4E, the medical professional speaks the free-form instruction "on April $12^{th}$ remind me to follow-up with John Cartales," and the free-form instruction is received by the virtual medical assistant for processing. The medical professional does not specify the year, but the virtual medical assistant may reasonably infer the year to be the current year, and proceed to set-up a reminder for Apr. 12, 2013. The virtual medical assistant may present the reminder to the medical professional and request that the medical professional confirm, either by presenting a touchable icon or other manually activated confirmation, processing a further free-form speech instruction, or both. Alternatively, the virtual medical assistant may set up the reminder and report details of the completed task without asking for confirmation from the medical professional.

FIG. 4F illustrates a medical professional utilizing dictation functionality to capture free-form narration in connection with a patient encounter. For example, the medical professional may say "Please take dictation for Jane Doe," and the virtual medical assistant may interpret this instruction as the medical professional wishing to provide a narrative regarding a patient encounter, such as a patient visit, with Jane Doe. The virtual medical assistant may instruct the medical professional to tap the microphone and beginning speaking the narrative. The free-from narrative may be captured by the device, received by the virtual medical assistant and processed to recognize the content of the dictation. The recognized dictation may be provided back to the user on the display via the virtual medical assistant application. According to some embodiments, the virtual medical assistant may merely receive the audio and transfer the audio to another system, e.g., a system that archives audio dictation for transcription either by a transcriptionist or by an offline batch automatic recognition system. According to some embodiments, the recognized dictation (e.g., recognized by ASR component 130) is transmitted to an EHR system to be included in the patient's electronic medical record. According to some embodiments, the recognized dictation is provided to an NLU component to extract medical facts to add the facts to the EHR system according to the structure of the database. According to some embodiments, the virtual medical assistant may infer some information about the dictation and provide this information to populate fields in an EHR system (e.g., the virtual medical assistant may infer the date from the statement "Regarding Tuesday's visit . . . " and may also populate patient name information by virtue of receiving the instruction "Please take dictation for Jane Doe.").

Figure 4H:
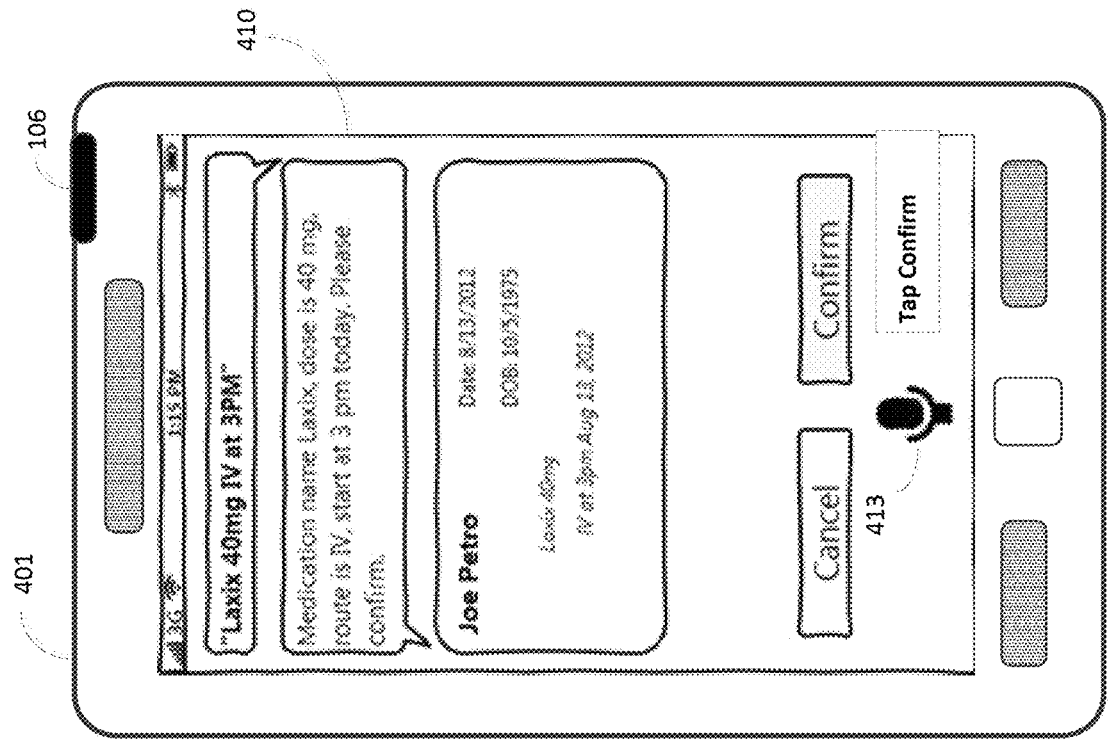
Figure 4G:
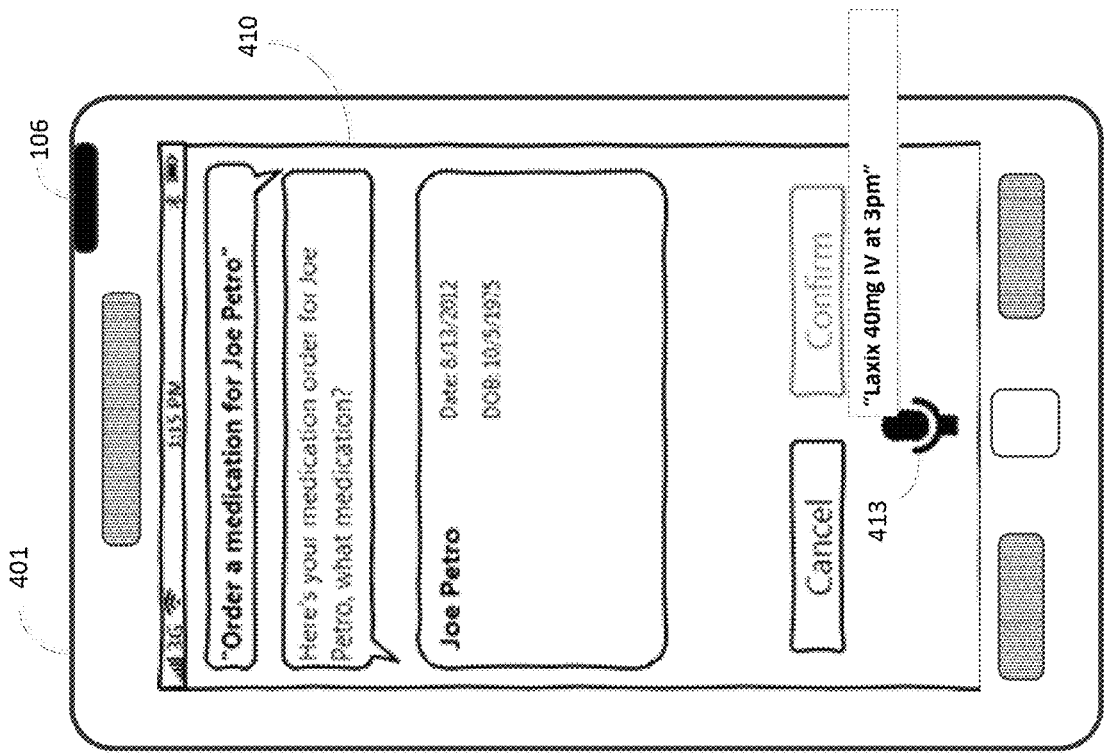

FIGS. 4G and 4H illustrate an example dialog between a virtual medical assistant, wherein the medical professional utilizes the virtual medical assistant to order medication for a patient. As shown in FIG. 4G, the medical professional speaks the free-form instruction: "Order a medication for Joe Petro," which is received by the virtual medical assistant application via the audio input capabilities of the mobile device. The virtual medical assistant application on the mobile device may then provide the free-form instruction to a medical understanding resource of the system for processing to recognize the medical professional's speech and understand the speech content. In this example, the virtual medical assistant understands that the medical professional would like to order a medication and recognizes that additional information is needed to complete the medical task of submitting a medication order.

To begin the process of obtaining further information, the medical virtual assistant formulates the response: "Here's your medication order for Joe Petro. What medication?" and presents the response to the medical professional. In this example, the virtual medical assistant, in its response to the free-form instruction, both queries the medical professional for further information and presents to the medical professional a medication order filled out with the information gleaned by the virtual medical assistant from the free-form instruction, which in the first instance consists primarily of the patient name and date of birth (which the virtual medical system may have obtained by accessing a EHR system, or other medical records system available to the virtual medical assistant). Presenting the medication order to the medical professional allows the medical professional to quickly confirm that the virtual medical assistant understood the instruction and has identified the correct patient so that the medical professional feels comfortable proceeding.

In the example illustrated in FIGS. 4G and 4H, in response to the query regarding the medication, the medical professional responds by saying: "Medication name Laxix, dose is 40 mg, route is IV, start at 3 pm today. Please confirm." The virtual medical assistant receives the free-form speech instruction and processes the speech to extract information needed to complete the medication order. In this example, the virtual medical assistant extracts the medication name, dose, route and time of administration and presents this information on the medication order for the medical professional to review. It should be appreciated that any of the responses provided by the virtual medical assistant may be rendered as audio either alone or to supplement a visual display of the response. The virtual medical assistant application also presents a confirmation icon to the medical professional so that the medical professional can confirm that the medication order is correct. While the medical professional explicitly requested confirmation, the virtual medical assistant may automatically await confirmation for any medical task where confirmation is appropriate and/or required, thus facilitating performance of medical tasks with fewer mistakes and avoiding medical error. The virtual medical assistant may be configured to always request confirmation or may dispense with confirmation for certain task unless the medical professional requests confirmation, as the aspects are not limited in this respect.

If the medical professional confirms that the medication order is correct (e.g., by tapping the "Confirm" icon, the virtual medical assistant may generate a medication order formatted to conform to a target ordering system (e.g., a desired CPOE system) and submit the order for processing by the CPOE system to complete the medication order. In the example in FIGS. 4G and 4H, the medical professional provided the needed information in a single response. However, if the virtual medical assistant required further information from the medical professional, the discourse with the medical professional may continue until the information needed to complete the order is received. Additionally, any other impediment identified by the virtual medical assistant, such as issues with drug interaction, dose or route incompatibility or any questions the virtual medical assistant has in connection with the medication order, may be worked out with the medical professional via an appropriate dialog exchange between the medical professional and the virtual medical assistant.

As discussed above, a virtual medical assistant may be configured to dialog with a medical professional by rendering responses (e.g., prompts, requests, inquiries, alerts, warnings, etc.) either visually or audibly. With respect to audibly rendering responses, the virtual medical assistant may employ speech synthesis techniques, either over a network or using local resources, to generate audio responses that can be rendered, for example, using one or more speakers coupled to the device hosting the virtual medical assistant or using a separate interface component. Providing audio responses may be used alone, or in combination with visual responses, or one or the other may be used depending on the circumstances, environment or medical professional preference.

Table 1 below illustrates an example discourse between a medical professional and a virtual medical assistant essentially conducted in audio to allow, for example, the exchange to take place without requiring the medical professional to visually focus on the device and/or in situations wherein the device being used by the medical professional to interact with the virtual medical assistant does not include display functionality, or the virtual medical assistant does not have access to display functionality of the device. In particular, the free-form instruction may be provided by the medical professional using speech and the responses from the virtual medical assistant may be rendered via audio using speech synthesis techniques and/or prerecorded speech. Such an audio mode may be preferable in certain circumstances such as when the medical professional's visual focus is trained elsewhere (e.g., while driving, performing a procedure or otherwise attending to a patient, etc.), when the display of the device hosting the virtual medical assistant makes visual responses difficult or otherwise problematic, or visual responses are not possible (e.g., the interface used by the medical professional does not include display capabilities such as a telephone call-in environment). An example discourse for ordering medication may proceed as follows.

TABLE 1

EXAMPLE AUDIBLE DIALOG

Medical professional: Write a medication order for John Doe, give Furosemide 40 mg po stat
Provider: CPOE medication order info: Patient is John Doe, Medication Name Furosemide, Dose 40 mg, Route is po, Priority is stat, Start Time is Now. What Medication form?
Medical professional: Form is pill
Provider: CPOE order information is complete: Patient is John Doe, Medication Name Furosemide, Dose 40 mg, Route is po, administration is pill form, Priority is stat, Start Time is Now.
Medical professional: Correct, please proceed to order.
Provider: There is a potential allergic reaction alert with this order. Do you want to change the order?
Medical professional: What is the problem?
Provider: The patient is allergic to penicillin, of category PCN Cephalospor for the reasons of anaphylaxis.

TABLE 1-continued

EXAMPLE AUDIBLE DIALOG

Medical professional: Override the alert, the patient is not truly allergic.
Provider: Okay, overriding the allergy alert with overriding reason that the patient is not truly allergic. Please speak your voice signature to override.
Medical professional: <Voice Signature>
Provider: Thank you, CPOE order for John Doe has been submitted, order number is #######. Do you wish to make another order?
Medical professional: Yes, order Levofloxacin 5000 mg IV for 3 days everyday dose now, then routine schedule times.
Provider: CPOE medication order for John Doe, Medication name Levoflaxin, dose 5000 mg, route IV, frequency every day for 3 days. Start dose now, then routine schedule times. Please confirm that this is correct and provide any special instructions?
Medical professional: Yes, correct. No special instructions.
Provider: The dose of 5000 mg is greater than recommended dose of 500 mg according to National Drug Data File recommendation. How would you like to proceed?
Medical professional: Override. The reason is a ABN kidney function.
Provider: Okay, overriding the min/max dose alert with overriding reason of ABN kidney function. Please say your voice signature to override.
Medical professional: <Voice Signature>
Provider: Thank you. Medication order for John Doe has been submitted, order number is #######. Do you wish to make another order?
Medical professional: Not right now.

It should be appreciated that the above discourse may also be implemented using visual responses (e.g., using any of the visual display techniques illustrated in FIGS. 4A-4H, or any other suitable display technique or format) and/or medical professional input may be received in ways other than speech (e.g., via keypad, touch icons, etc.), as the example in Table 1 is merely illustrative of one possible way of conducting a dialog with a medical professional that may be suitable (or advantageous) in certain situations, while visual display may be used and/or preferred in other situations.

The example discourse illustrated in Table 1 demonstrates the use of dialog and inference techniques to discourse with the medical professional to understand and help complete the medical task of placing a medication order. In particular, in multiple instances, the virtual medical assistant provided responses to the medical professional to obtain further information regarding the medication order (e.g., request missing information such as medication form, inquire as to special instructions, etc.) and/or alert the medical professional to conflicts in connection with the medication order (e.g., drug-allergy alert, min/max dose alert).

In addition, in the example discourse illustrated in Table 1, the virtual medical assistant obtains information by inference from previously received instruction and/or information obtained as a result of previously received instruction. For example, the medical professional's second medication order (e.g., Levofloxacin) did not include the name of the patient but the virtual medical assistant inferred that the patient was the same as for the previous order.

A virtual medical assistant may be configured with security measures such as any one or combination of password protection, voice verification/authentication, signature verification/authentication, etc. to verify and/or confirm that a user providing free-form instruction is authorized to perform one or more medical tasks specified in free-form instruction received from the user. Any suitable security techniques may be utilized, as the aspects are not limited in this respect.

Figure 5:
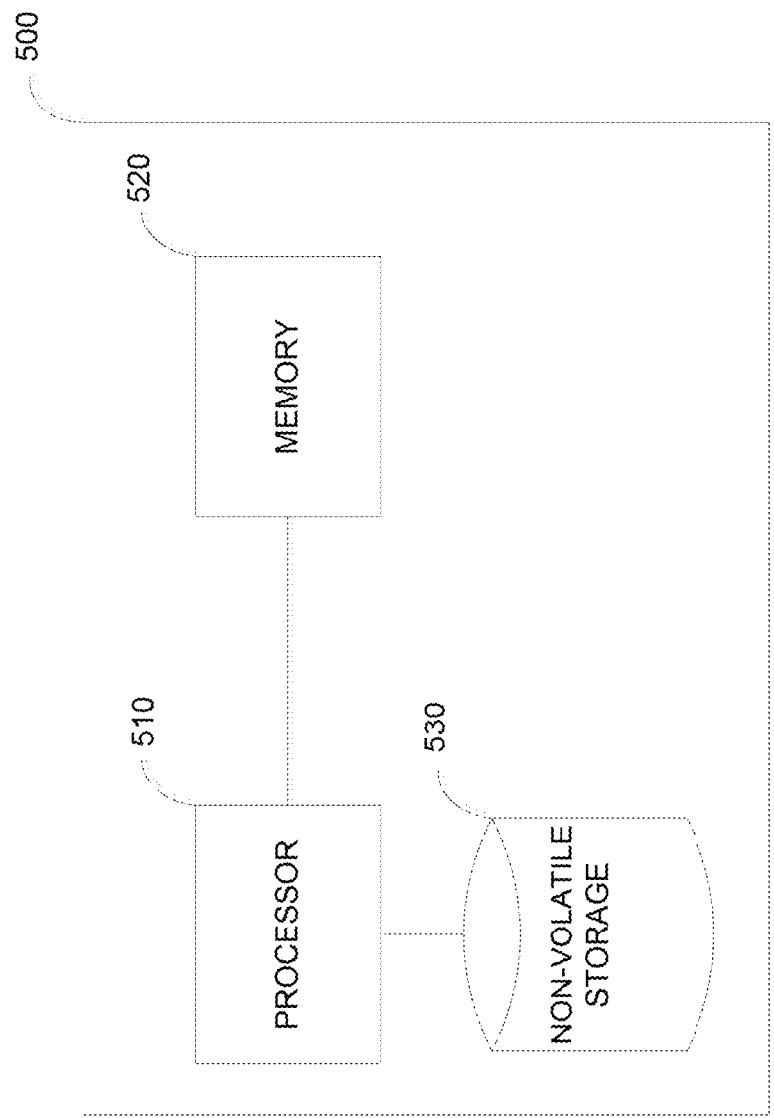
FIG. 5 is an exemplary computer system on which techniques described herein may be implemented, in accordance with some embodiments.

An illustrative implementation of a computer system 500 that may be used to implement one or more virtual medical assistant techniques described herein is shown in FIG. 5. Computer system 500 may include one or more processors 510 and one or more non-transitory computer-readable storage media (e.g., memory 520 and one or more non-volatile storage media 530). The processor 510 may control writing data to and reading data from the memory 520 and the non-volatile storage device 530 in any suitable manner, as the aspects of the invention described herein are not limited in this respect. Processor 510, for example, may be a processor on a mobile device.

To perform functionality and/or techniques described herein, the processor 510 may execute one or more instructions stored in one or more computer-readable storage media (e.g., the memory 520, storage media, etc.), which may serve as non-transitory computer-readable storage media storing instructions for execution by processor 510. Computer system 500 may also include any other processor, controller or control unit needed to route data, perform computations, perform I/O functionality, etc. For example, computer system 500 may include any number and type of input functionality to receive data and/or may include any number and type of output functionality to provide data, and may include control apparatus to perform I/O functionality.

In connection with identifying task(s) specified in free-form instruction, one or more programs configured to receive free-form instruction, process the instruction or otherwise execute functionality described herein may be stored on one or more computer-readable storage media of computer system 500. In particular, some portions or all of a virtual medical assistant may be implemented as instructions stored on one or more computer-readable storage media. Processor 510 may execute any one or combination of such programs that are available to the processor by being stored locally on computer system 500 or accessible over a network. Any other software, programs or instructions described herein may also be stored and executed by computer system 500. Computer system 500 may represent the computer system on a host device on which a virtual medical assistant application is installed and/or may represent the computer system on which any one or combination of network resources are implemented (e.g., any one or combination of components forming a virtual medical assistant, or other network resource). Computer system 500 may be implemented as a standalone computer, server, part of a distributed computing system, and may be connected to a network and capable of accessing resources over the network and/or communicate with one or more other computers connected to the network (e.g., computer system 500 may be part of the network resources available to a virtual medical assistant).

The terms "program" or "software" are used herein in a generic sense to refer to any type of computer code or set of processor-executable instructions that can be employed to program a computer or other processor to implement various aspects of embodiments as discussed above. Additionally, it should be appreciated that according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which multiple examples have been provided. The acts performed as part of each process may be ordered in any suitable way. Accordingly, embodiments may be constructed in which acts are performed in an order different than illustrated, which may include performing some acts concurrently, even though shown as sequential acts in illustrative embodiments.

All definitions, as defined and used herein, should be understood to control over dictionary definitions, and/or ordinary meanings of the defined terms.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the techniques described herein in detail, various modifications, and improvements will readily occur to those skilled in the art. Such modifications and improvements are intended to be within the spirit and scope of the disclosure. Accordingly, the foregoing description is by way of example only, and is not intended as limiting. The techniques are limited only as defined by the following claims and the equivalents thereto.

The invention claimed is:

1. A host device for improving safety of performing one or more medical tasks by providing access to a medical domain-specific virtual clinical assistant, the host device being capable of accessing at least one network, the host device comprising:
   at least one microphone configured to receive free-form speech instruction from a medical professional; and
   at least one speaker configured to output audio to the medical professional; and at least one processor configured to:
      provide, to the medical professional, at least one graphical user interface to the virtual clinical assistant;
      using a dialog component, receive the free-form speech instruction from the medical professional via the at least one microphone;
      provide the free-form speech instruction for speech processing, including automatic speech recognition, at least by transmitting the free-form speech instruction over the at least one network to an automatic speech recognition component to recognize at least a portion of the free-form speech instruction;
      provide the recognized free-form speech instruction to a natural language understanding component to assist in automatically identifying from the free-form speech instruction at least one medical task to be performed;
      identify, using the free-form speech instruction, medical information to be obtained from a medical information resource via the at least one network; and using the dialog component, establish a dialog between the virtual clinical assistant and the medical professional at least by:
providing, via the at least one speaker, at least one query spoken to the medical professional regarding the free-form speech instruction prior to the at least one medical task being performed;
displaying the at least one query on the graphical user interface; and
receiving first information from the medical professional, via the at least one microphone, responsive to the at least one query to improve the safety of performing the at least one medical task.

2. The host device of claim 1, wherein the free-form speech instruction is processed by the natural language understanding component to identify information expressed in the free-form speech instruction indicating an intent to perform the at least one medical task.

3. The host device of claim 2, wherein the at least one processor is configured to obtain an identification of at least one impediment to performing the at least one medical task, and wherein the at least one query is provided to the medical professional using the dialog component to facilitate overcoming the at least one impediment.

4. The host device of claim 3, wherein the identified at least one impediment includes one or more impediments selected from a group consisting of: an identification of information missing from the free-form speech instruction needed to perform the at least one medical task, at least one ambiguity in connection with performing the at least one medical task, an inability to identify the at least one medical task with sufficient certainty, and one or more conflicts in connection with performing the at least one medical task.

5. The host device of claim 1, wherein the at least one medical task identified from the free-form speech instruction includes a request to order an orderable item.

6. The host device of claim 5, wherein the identified request to order the orderable item includes an order selected from the group consisting of: a medication order, a procedure order, a lab order, a diagnostic test order, an appointment order, a referral order, and a consultation order.

7. The host device of claim 6, wherein the identified at least one impediment includes one or more conflicts including at least one conflict between the orderable item and information identified in the free-form speech instruction and/or patient information obtained from an electronic medical record associated with the patient, and wherein providing the at least one query comprises providing an alert to the medical professional regarding the at least one conflict using the dialog component.

8. The host device of claim 6, wherein the at least one processor is configured to:
infer the at least some information at least by inferring at least some information needed to complete the order of the orderable item; and
submit an electronic order for the orderable item.

9. The host device of claim 1, wherein the at least one processor is configured to:
automatically identify at least one impediment o performing the at least one medical task; and
automatically infer at least some information needed to overcome the at least one impediment.

10. The host device of claim 9, wherein
the free-form speech instruction is a second free-form speech instruction;
the at least some information is inferred, at least in part, from a first free-form speech instruction received before the second free-form speech instruction, inforrn.ation obtained responsive to the first free-form speech instruction, an electronic medical record associated with a patient, and/or the medical information resource accessible over the at least one network.

11. The host device of claim 10, wherein the first free-form speech instruction comprises a request from the medical professional to view patient information for a patient, and wherein the at least one processor is configured to infer the at least sonic information from the patient information received responsive to the free-form speech instruction and/or from an electronic medical record associated with the patient identified in the free-form speech instruction.

12. The host device of 9, wherein
the free-form speech instruction is a second free-form speech instruction;
the at least some information is inferred, at least in part, from a first free-form speech instruction received before the second free-form speech instruction, information obtained responsive to the first free-form speech instruction, an electronic medical record associated with a patient, and/or the medical information resource accessible over the at least one network.

13. A system for improving safety of performing one or more medical tasks by providing access to a medical domain-specific virtual clinical assistant, the system comprising:
a host device configured to access at least one network; and at least one server connected to the at least one network, wherein the host device comprises:
at least one microphone configured to receive free-form speech instruction from a medical professional;
at least one speaker configured to output audio to the medical professional; and at least one processor configured to:
provide, to the medical professional, at least one graphical user interface to the virtual clinical assistant, wherein the virtual clinical assistant is hosted at least in part by the at least one server;
using a dialog component; receive the free-form speech instruction from the medical professional via the at least one microphone;
provide the free-form speech instruction for speech processing at least in part on the at least one server, including automatic speech recognition, at least by transmitting the free-form speech instruction over the at least one network to an automatic speech recognition component to recognize at least a portion of the free-form speech instruction;
provide the recognized free-form speech instruction to a natural language understanding component to assist in automatically identifying from the free-form speech instruction at least one medical task to be performed, wherein the at least one server is configured to perform the speech processing including the automatic speech recognition based on at least one statistical model;
identify medical information relating to content of the free-form speech instruction to be obtained from a medical information resource via the at least one network; and
using the dialog component, establish a dialog between the virtual clinical assistant and the medical professional at least by:
providing, via the at least one speaker, at least one query spoken to the medical professional regarding the free-form speech instruction prior to the at least one medical task being performed;

displaying the at least one query on the graphical user interface; and receiving first information from the medical professional, via the at least one microphone, responsive to the at least one query to improve the safety of performing the at least one medical task.

14. A computer-implemented method comprising:

providing, by a processer of a host device, a graphical user interface displaying a virtual clinical assistant, wherein the virtual clinical assistant is hosted at least in part by a server connected to a network;

receiving, using a dialog component of the host device via a microphone, free-form speech input from a medical professional;

transmitting, by the host device via the network, the free-form speech input to an automatic speech recognition component f©r speech processing, wherein the automatic speech recognition component is implemented on the server and is configured to perform the speech processing: including automatic speech recognition based on at least one statistical model;

receiving, by the host device from the automatic speech recognition component, recognized free-form speech instruction from the free-form speech input;

providing the recognized free-form speech instruction to a natural language understanding component implemented on the host device to assist in automatically identifying from the recognized free-form speech instruction at least one medical task to be performed and an associated instruction to perform the medical task;

identifying medical information relating to content of the recognized free-form speech instruction and the at least one medical task to be performed;

obtaining the identified medical information from a medical information resource via the network; and establishing, using the dialog component, a dialogue between the virtual clinical assistant and the medical professional at least by:

providing, via a speaker of the host device, at least one query spoken to the medical professional by the virtual clinical assistant regarding the free-form speech instruction prior to the at least one medical task being performed;

displaying the at least one query on the graphical user interface; and responsive to the at least one query spoken by the virtual clinical assistant, receiving first information from the medical professional to improve safety of performing the at least one medical task.

15. The method of claim 14, wherein the recognized free-form speech instruction is processed by the natural language understanding component to identify information expressed in the free-form speech input indicating an intent to perform the at least one medical task.

16. The method of claim 14, wherein the processor is configured to obtain an identification of at least one impediment to performing the at least one medical task, and wherein the at least one query is provided to the medical professional using the dialog component to facilitate overcoming the at least one impediment.

17. The method of claim 14, wherein the natural language understanding component includes at least one knowledge representation model that captures medical domain semantic knowledge.

18. The method of claim 14, wherein establishing the dialogue between the virtual clinical assistant and the medical professional further comprises:

identifying an associated instruction within the first information received from the medical professional; and providing the associated instruction to at least one computer-implemented process to perform the at least one medical task.

19. The method of claim 14, further comprising:

automatically identifying at least one impediment to performing the at least one medical task; and inferring at least some information needed to overcome the at least one impediment.

20. The method of claim 19, wherein the free-form speech instruction is a second free-form speech instruction, and the at least some information inferred is from a first free-form speech instruction received before the second free-from speech instruction, information obtained responsive to the first free-form speech instruction, an electronic medical record associated with a patient, and/or the medical information resource accessible over the network.

* * * * *